US009962591B2

United States Patent
Sato

(10) Patent No.: US 9,962,591 B2
(45) Date of Patent: May 8, 2018

(54) MOTION ANALYSIS METHOD, PROGRAM, AND MOTION ANALYSIS DEVICE

(71) Applicant: SEIKO EPSON CORPORATION, Tokyo (JP)

(72) Inventor: Masafumi Sato, Hara-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 179 days.

(21) Appl. No.: 14/745,944

(22) Filed: Jun. 22, 2015

(65) Prior Publication Data
US 2016/0001127 A1 Jan. 7, 2016

(30) Foreign Application Priority Data

Jul. 2, 2014 (JP) .................. 2014-136847

(51) Int. Cl.
*A63B 24/00* (2006.01)
*A63B 69/36* (2006.01)
*A61B 5/00* (2006.01)
*A61B 5/11* (2006.01)

(52) U.S. Cl.
CPC ............ *A63B 69/3632* (2013.01); *A61B 5/11* (2013.01); *A61B 5/68* (2013.01); *A61B 5/6895* (2013.01)

(58) Field of Classification Search
CPC .................. A63B 24/0003; A63B 69/3632
See application file for complete search history.

(56) References Cited

U.S. PATENT DOCUMENTS

| 8,465,376 B2* | 6/2013 | Bentley | A63B 24/0006 473/219 |
| 2005/0215336 A1* | 9/2005 | Ueda | A63B 24/0003 473/131 |
| 2009/0208061 A1 | 8/2009 | Matsumoto et al. | |
| 2014/0073446 A1* | 3/2014 | Davenport | A63B 24/0006 473/223 |
| 2014/0200094 A1* | 7/2014 | Parke | A63F 13/00 473/223 |
| 2014/0379293 A1 | 12/2014 | Sato | |
| 2015/0072797 A1* | 3/2015 | Sakyo | A63B 24/0006 473/223 |

FOREIGN PATENT DOCUMENTS

| JP | 2008-073210 A | 4/2008 |
| JP | 2009-020897 A | 1/2009 |
| JP | 2015-002910 A | 1/2015 |

* cited by examiner

*Primary Examiner* — Michael Dennis
(74) *Attorney, Agent, or Firm* — Oliff PLC

(57) ABSTRACT

A motion analysis method includes: specifying a first axis along a longitudinal direction of a shaft of a golf club when a user is at a standstill using an output of a sensor unit; and estimating a prescribed position between head and chest of the user when the user is at a standstill using the output of the sensor unit and body information of the user, and specifying a second axis which connects the estimated prescribed position and a hitting position.

12 Claims, 13 Drawing Sheets

MOTION ANALYSIS METHOD, PROGRAM, AND MOTION ANALYSIS DEVICE

BACKGROUND

1. Technical Field

The present invention relates to a motion analysis method, a program, and a motion analysis device which analyze the motion of a user.

2. Related Art

JP-A-2009-20897 discloses a technology that performs display by photographing a golf swing motion using a camera or the like from the back of a user, specifying a swing plane from a photographed image, displaying the swing plane, and measuring the area of the swing plane. The swing plane is a plane in which a line segment including an arm, a club shaft, and a club head (or a club shaft and a club head) moves during a golf swing motion and remains as a locus. Generally, when viewed from the back of the swing, it is determined that swing is good if the swing plane does not have an area as much as possible and is close to a segment. Accordingly, according to the technology of JP-A-2009-20897, the user is capable of quantitatively knowing whether the swing is good or bad from information of the area of the swing plane.

However, even when the area of the swing plane is small, there is a case in which the user hits a hook or a slice according to a swing path, and thus the small area of the swing plane is not necessarily a good swing. Here, when directing golf swing, there is a case in which indexes, such as a shaft plane and a hogan plane, are used. The shaft plane is a plane that includes the longitudinal direction of the shaft of a golf club at address (standstill state) in golf and a target line (ball-hitting direction), and the hogan plane is a plane that includes a virtual line, which connects the peripheries of the shoulder (the joint or the like of the shoulder and the neck) of a golfer at address in golf and the head of the golf club (or a ball), and a target line (target ball-hitting direction). A region which is interposed by the shaft plane and the hogan plane is called a V zone, and it is known that the user hits a straight if the locus of the golf club is included in the V zone when down swing is performed. Accordingly, it is possible to evaluate good or bad of swing based on whether or not the locus of the golf club is included in the V zone when down swing is performed. However, a technology that accurately presents the shaft plane and the hogan plane to the user has not been proposed yet.

SUMMARY

An advantage of some aspects of the invention is to provide a motion analysis method, a program and a motion analysis device which are capable of accurately presenting information for evaluating good or bad of swing, compared to the related art.

The invention can be implemented as the following forms or application examples.

Application Example 1

A motion analysis method according to this application example includes: specifying a first axis along a longitudinal direction of a shaft section of sporting equipment when a user is at a standstill using an output of an inertial sensor; and estimating a prescribed position between head and chest of the user when the user is at a standstill using the output of the inertial sensor and body information of the user, and specifying a second axis which connects the estimated prescribed position and a hitting position.

Sporting equipment includes, for example, equipment, which is used to hit a ball, such as a golf club, a tennis racket, a baseball bat, a hockey stick, or the like. A shaft section is a part of a grip of the sporting equipment. In sporting equipment, which includes a grip part, the grip part is included in the shaft section.

The inertial sensor may be a sensor which is capable of measuring the amount of inertia, such as acceleration or angular velocity, and may be, for example, an Inertial Measurement Unit (IMU) which is capable of measuring the acceleration or the angular velocity. In addition, the inertial sensor may be attached to, for example, the sporting equipment or a part of the user, and may be detachable from the sporting equipment or the user. Otherwise, the inertial sensor may be embedded into the sporting equipment and fixed to the sporting equipment such that it is difficult to be removed from the sporting equipment.

In the motion analysis method according to this application example, the user is capable of objectively recognizing a posture at a standstill from the positions and inclinations of a first axis and a second axis and the size of a space between the first axis and the second axis, and is capable of recognizing the positional relationship between the path of assuming swing, the first axis, and the second axis, and thus it is possible to accurately evaluate good or bad of swing, compared to the related art.

In addition, in the motion analysis method according to this application example, the first axis and the second axis are specified using the inertial sensor. Therefore, it is not necessary to use a large scale device such as a camera, and restrictions on place in which the motion analysis is performed are small. Further, the second axis is specified using the body information of the user, and thus it is possible to commonly use the output of the inertial sensor to specify the first axis and specify the second axis.

Application Example 2

The motion analysis method according to the application example described above may further include calculating a position of a grip end of the sporting equipment using the output of the inertial sensor, and the specifying of the second axis may include estimating the prescribed position using the position of the grip end and a length of an arm of the user based on the body information.

In the motion analysis method according to this application example, attention is paid to a fact that the distance between the prescribed position between the head and the chest of the user and the position of the grip end of the sporting equipment is related to the length of the arm of the user, and thus it is possible to specify the second axis according to the figure of the user using the position of the grip end and the length information of the arm of the user.

Application Example 3

In the motion analysis method according to the application example described above, the output of the inertial sensor may include acceleration information, the motion analysis method may further include calculating an angle of inclination for a horizontal plane of the shaft section using the acceleration information when the user is at a standstill, and the specifying of the first axis may include specifying the first axis using the angle of inclination and information of a length of the shaft section.

In the motion analysis method according to this application example, it is possible to calculate an angle of inclination of the shaft section of the sporting equipment using a fact that the inertial sensor detects only acceleration of gravity when the user is at a standstill, and it is possible to specify the orientation of the first axis based on the angle of inclination.

Application Example 4

In the motion analysis method according to the application example described above, the body information may be the length of the arm of the user.

Application Example 5

In the motion analysis method according to this application example, the prescribed position may be on a line segment which connects both shoulders of the user.

Application Example 6

The motion analysis method according to the application example described above may further include, when a target ball-hitting direction is set to a third axis: specifying a first virtual plane which includes the first axis and the third axis; and specifying a second virtual plane which includes the second axis and the third axis.

In the motion analysis method according to this application example, the user is capable of objectively recognizing the posture at a standstill from the positions and inclinations of a first virtual plane and a second virtual plane and the size of a space between the first virtual plane and the second virtual plane, and is capable of recognizing the positional relationship between the path of the assuming swing, the first virtual plane and the second virtual plane, and thus it is possible to accurately evaluate good or bad of swing, compared to the related art.

Application Example 7

In the motion analysis method according to the application example described above, the sporting equipment may be provided with a ball-hitting surface, and the third axis may be an axis in a direction which is perpendicular to the ball-hitting surface when the user is at a standstill.

In the motion analysis method according to this application example, it is assumed that the user is at a standstill with a posture in which the target ball-hitting direction is perpendicular to the ball-hitting surface of the sporting equipment, and thus it is possible to specify a third axis which indicates the target ball-hitting direction using the output of the inertial sensor.

Application Example 8

In the motion analysis method according to the application example described above, the specifying of the first virtual plane may include calculating a width of the first virtual plane using the length of the shaft section and the length of the arm of the user based on the body information.

In the motion analysis method according to this application example, the width of the first virtual plane is calculated using the length of the shaft section of the sporting equipment and the length of the arm of the user, and thus it is possible to specify the first virtual plane having a size which is appropriate to swing evaluation in which the size of the swing path of the user is considered.

Application Example 9

In the motion analysis method according to the application example described above, the specifying of the second virtual plane may include calculating a width of the second virtual plane using the length of the shaft section and the length of the arm of the user based on the body information.

In the motion analysis method according to this application example, the width of the second virtual plane is calculated using the length of the shaft section of the sporting equipment and the length of the arm of the user, and thus it is possible to specify the second virtual plane having a size which is appropriate to swing evaluation in which the size of the swing area of the user is considered.

Application Example 10

The motion analysis method according to the application example described above may further include acquiring information of locus of the sporting equipment based on swing performed by the user; and determining whether or not the locus is included between the first axis and the second axis.

In the motion analysis method according to this application example, it is possible for the user to accurately and easily evaluate good or bad of swing based on the result of determination whether or not the locus of the sporting equipment based on swing is included in the space between the first axis and the second axis.

Application Example 11

The motion analysis method according to the application example described above may further include acquiring information of locus of the sporting equipment based on swing performed by the user; and determining whether or not the locus is included between the first virtual plane and the second virtual plane.

In the motion analysis method according to this application example, it is possible for the user to objectively and easily evaluate good or bad of swing based on the result of determination whether or not the locus of the sporting equipment based on swing is included in the space between the first virtual plane and the second virtual plane.

Application Example 12

The motion analysis method according to the application example described above may further include acquiring information of locus of the sporting equipment based on swing performed by the user; and generating image data which includes the first axis, the second axis, and the locus.

In the motion analysis method according to this application example, the user is capable of determining whether or not the locus of the sporting equipment based on swing is included between the first axis and the second axis from an image, and thus it is possible to objectively and easily evaluate good or bad of swing.

Application Example 13

In the motion analysis method according to the application example described above, the sporting equipment may be a golf club.

In the motion analysis method according to this application example, it is possible for the user to accurately evaluate good or bad of golf swing, compared to the related art.

Application Example 14

A program according to this application example causes a computer to specify a first axis along a longitudinal direction of a shaft section of sporting equipment when a user is at a standstill using an output of an inertial sensor; and estimate a prescribed position between head and chest of the user when the user is at a standstill using the output of the inertial sensor and body information of the user, and specify a second axis which connects the estimated prescribed position and a hitting position.

In the program according to this application example, the user is capable of objectively recognizing a posture at a standstill from the positions and inclinations of a first axis and a second axis and the size of a space between the first axis and the second axis, and is capable of recognizing the positional relationship between the path of assuming swing, the first axis, and the second axis, and thus it is possible to accurately evaluate good or bad of swing, compared to the related art.

In addition, in the program according to this application example, the first axis and the second axis are specified using the inertial sensor. Therefore, it is not necessary to use a large scale device such as a camera, and restrictions on place in which the motion analysis is performed are small. Further, the second axis is specified using the body information of the user, and thus it is possible to commonly use the output of the inertial sensor to specify the first axis and specify the second axis.

Application Example 15

A motion analysis device according to this application example includes: a first specification unit that specifies a first axis along a longitudinal direction of a shaft section of sporting equipment when a user is at a standstill using an output of an inertial sensor; and a second specification unit that estimates a prescribed position between head and chest of the user when the user is at a standstill using the output of the inertial sensor and body information of the user, and specifies a second axis which connects the estimated prescribed position and a hitting part position.

In the motion analysis device according to this application example, the user is capable of objectively recognizing a posture at a standstill from the positions and inclinations of a first axis and a second axis and the size of a space between the first axis and the second axis, and is capable of recognizing the positional relationship between the path of assuming swing, the first axis, and the second axis, and thus it is possible to accurately evaluate good or bad of swing, compared to the related art.

In addition, in the motion analysis device according to this application example, the first axis and the second axis are specified using the inertial sensor. Therefore, it is not necessary to use a large scale device such as a camera, and restrictions on place in which the motion analysis is performed are small. Further, the second axis is specified using the body information of the user, and thus it is possible to commonly use the output of the inertial sensor to specify the first axis and specify the second axis.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described with reference to the accompanying drawings. Meanwhile, the embodiments which are described below do not unfairly limit the content of the invention disclosed in the appended claims. In addition, all configurations which are described below are not the essential components of the invention.

Hereinafter, a motion analysis system (motion analysis device) which performs golf swing analysis will be described as an example.

1. Motion Analysis System 1-1. Outline of Motion Analysis System

Figure 1:
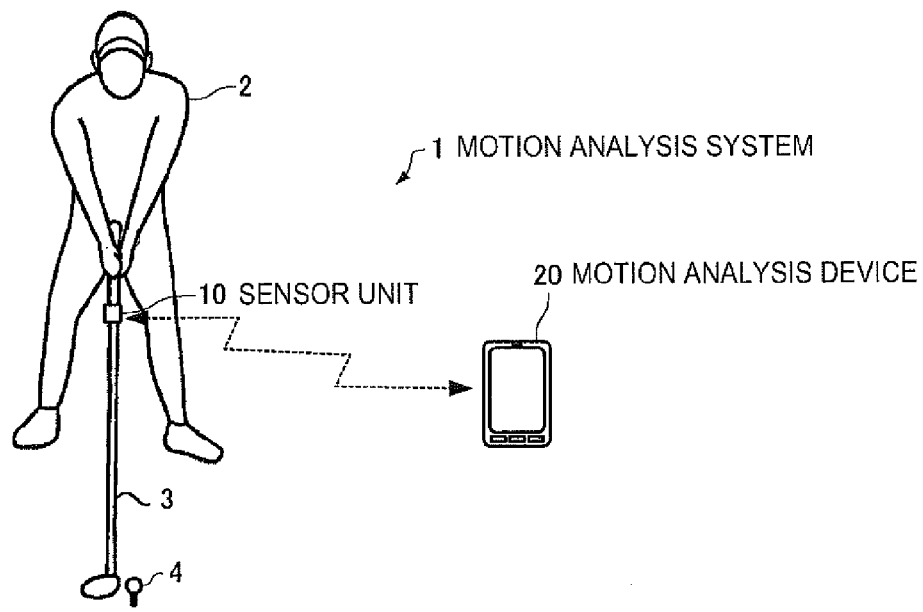
FIG. 1 is an explanatory view illustrating the outline of a motion analysis system according to an embodiment.

FIG. 1 is a diagram illustrating the outline of a motion analysis system according to an embodiment. A motion analysis system 1 according to the embodiment includes a sensor unit 10 (an example of an inertial sensor) and a motion analysis device 20.

The sensor unit 10 is capable of measuring acceleration, which is generated in each of the axial directions of 3 axes, and angular velocity which is generated around each of the 3 axes, and is mounted on a golf club 3 (an example of sporting equipment).

Figure 2:
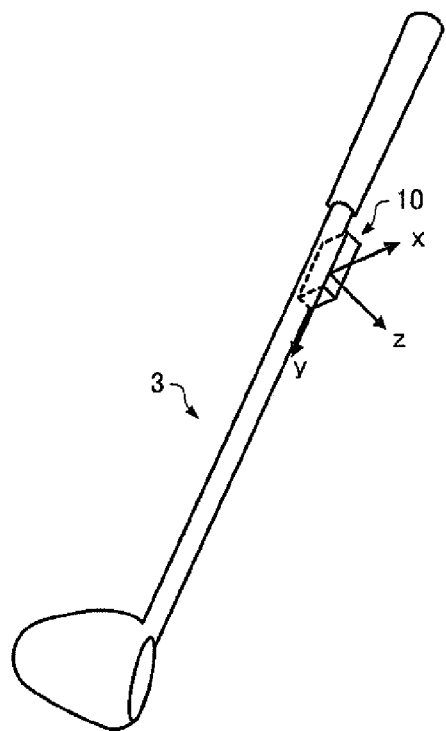
FIG. 2 is a diagram illustrating an example of the installation position and orientation of a sensor unit.

In the embodiment, as illustrated in FIG. 2, the sensor unit 10 is attached to a part of the shaft of the golf club 3 while one of 3 detection axes (an x axis, a y axis, and a z axis), for example, the y axis, is adjusted to the longitudinal direction of a shaft. Preferably, the sensor unit 10 is attached to a position which is close to a grip part where it is difficult to transmit a shock generated when a ball is hit and where it does not get centrifugal force generated when swing is performed. The shaft is a part of the handle excepting the head of the golf club 3 and includes the grip part.

Figure 3:
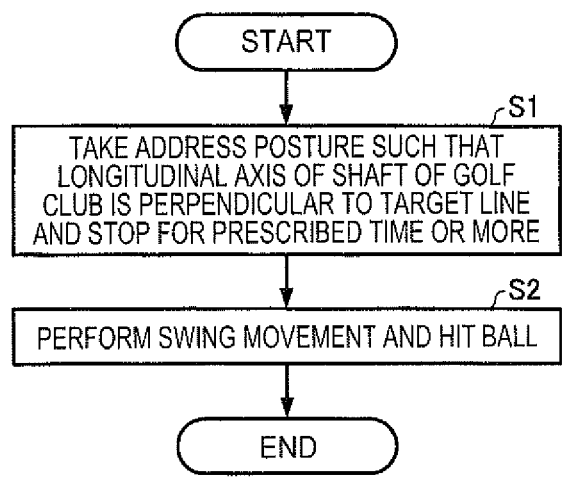
FIG. 3 is a flowchart illustrating the sequence of a movement performed by a user in the embodiment.

A user 2 hits a golf ball 4 according to a sequence which is determined in advance, that is, performs a swing movement. FIG. 3 is a flowchart illustrating the sequence of movement which is performed by the user 2. As illustrated in FIG. 3, the user 2 first grips the golf club 3, takes an address posture such that the longitudinal axis of the shaft of the golf club 3 is perpendicular to a target line (target ball-hitting direction), and stops for a prescribed time or more (for example, 1 or more seconds) (S1). Subsequently, the user 2 performs the swing movement, and hits the golf ball 4 (S2).

While the user 2 performs movement of ball hitting the golf ball 4 according to the sequence illustrated in FIG. 3, the sensor unit 10 measures 3 axial accelerations and 3 axial angular velocities during a prescribed period (for example, 1 ms), and sequentially transmits measurement data to the motion analysis device 20. The sensor unit 10 may immediately transmit the measurement data, or may store the measurement data in an inner memory and then transmit the measurement data at desired timing such as after the swing movement of the user 2 ends. The communication between the sensor unit 10 and the motion analysis device 20 may be wireless communication or wired communication. Otherwise, the sensor unit 10 may store the measurement data in a detachable recording medium, such as a memory card, and the motion analysis device 20 may read the measurement data from the recording medium.

The motion analysis device 20 analyzes motion, which is made in such a way that the user 2 hits a ball using the golf club 3, using the data measured by the sensor unit 10. More specifically, in the embodiment, the motion analysis device 20 specifies a shaft plane, which is a first virtual plane when the user 2 is at a standstill (at address), and a hogan plane, which is a second virtual plane, using the data measured by the sensor unit 10. Further, after the user 2 starts the swing movement, the motion analysis device 20 calculates the locus of the golf club 3 on swing, and determines whether the locus of the golf club 3 until the ball is hit on the swing is included in a space called a V zone between the shaft plane and the hogan plane. In addition, the motion analysis device 20 generates the locus of the golf club 3 on the swing of the user 2 and image data which includes the shaft plane and the hogan plane, and displays an image according to the image data on the display unit (display). The motion analysis device 20 may be, for example, a mobile terminal, such as a smart phone, or a personal computer (PC).

Figure 4:
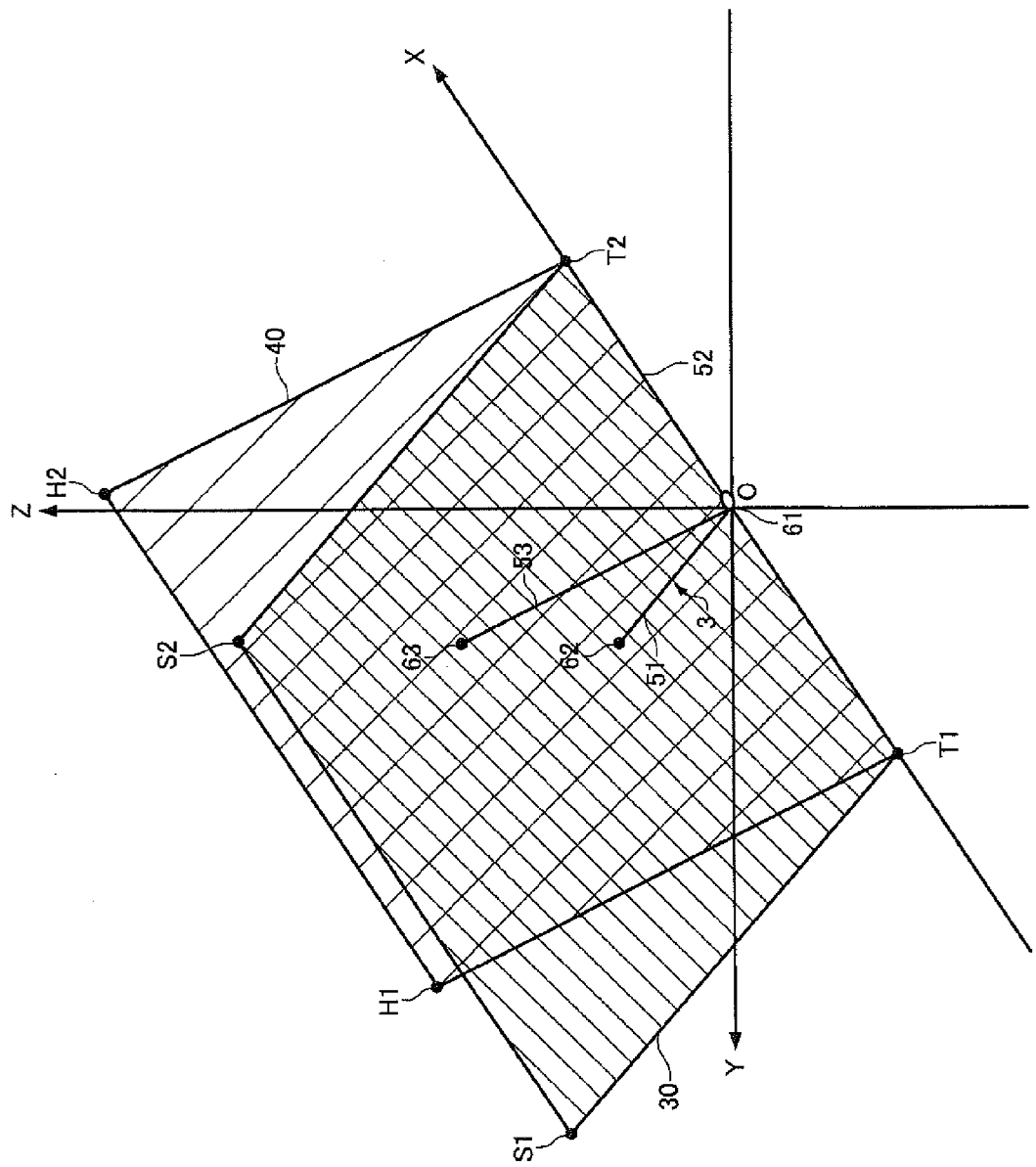
FIG. 4 is a diagram illustrating a shaft plane and a hogan plane.

FIG. 4 is a diagram illustrating the shaft plane and the hogan plane when the user 2 is at address according to the embodiment. In the embodiment, an XYZ coordinate system (global coordinate system), in which a target line indicative of a target ball-hitting direction is an X axis, an axis on a horizontal plane which is perpendicular to the X axis is a Y axis, and a vertical upper direction (the reverse direction of direction of acceleration of gravity) is a Z axis, is defined, and the X axis, the Y axis, and the Z axis are described in FIG. 4.

As illustrated in FIG. 4, in the embodiment, the shaft plane 30 acquired when the user 2 is at address is a virtual plane which includes a first line segment 51 as a first axis along the longitudinal direction of the shaft of the golf club 3, and a third line segment 52 as a third axis indicative of the target ball-hitting direction, and in which T1, T2, S1, S2 are set to 4 apexes. In the embodiment, the position 61 of the head (hitting part) of the golf club 3 is set to the origin O (0, 0, 0) of the XYZ coordinate system, and the first line segment 51 is a line segment which connects the position 61 (origin O) of the head of the golf club 3 to the position 62 of the grip end. In addition, the third line segment 52 is a line segment of a length TL which includes both ends T1 and T2 and the origin O as a middle point on the X axis. When the user 2 performs the movement in step S1 of FIG. 3 at address, the shaft of the golf club 3 is perpendicular to the target line (X axis), and thus the third line segment 52 is a line segment which is at right angles to the longitudinal direction of the shaft of the golf club 3, that is, a line segment which is at right angles to the first line segment 51. The shaft plane 30 is specified by calculating each of the coordinates of the 4 apexes T1, T2, S1, and S2 in the XYZ coordinate system. A method of calculating each of the coordinates of T1, T2, S1, and S2 will be described later.

In addition, as illustrated in FIG. 4, in the embodiment, the hogan plane 40 is a virtual plane which includes a third line segment 52 and a second line segment 53 as a second axis, and in which T1, T2, H1, H2 are set to 4 apexes. In the embodiment, the second line segment 53 is a line segment which connects a prescribed position 63 (for example, the position of the base of the neck or the position of either right or left shoulder) on a line segment, which connects both shoulders of the user 2, to the position 62 (an example of the ball hitting position) of the head (hitting part) of the golf club 3. However, the second line segment 53 may be a line segment which connects the prescribed position 63 and the position of the ball 4 (an example of the ball hitting position). The hogan plane 40 is specified by calculating each of the coordinates of the 4 apexes T1, T2, H1, and H2 in the XYZ coordinate system. A method of calculating each of the coordinates of T1, T2, H1, and H2 will be described later.

1-2. Configuration of Motion Analysis System

Figure 5:
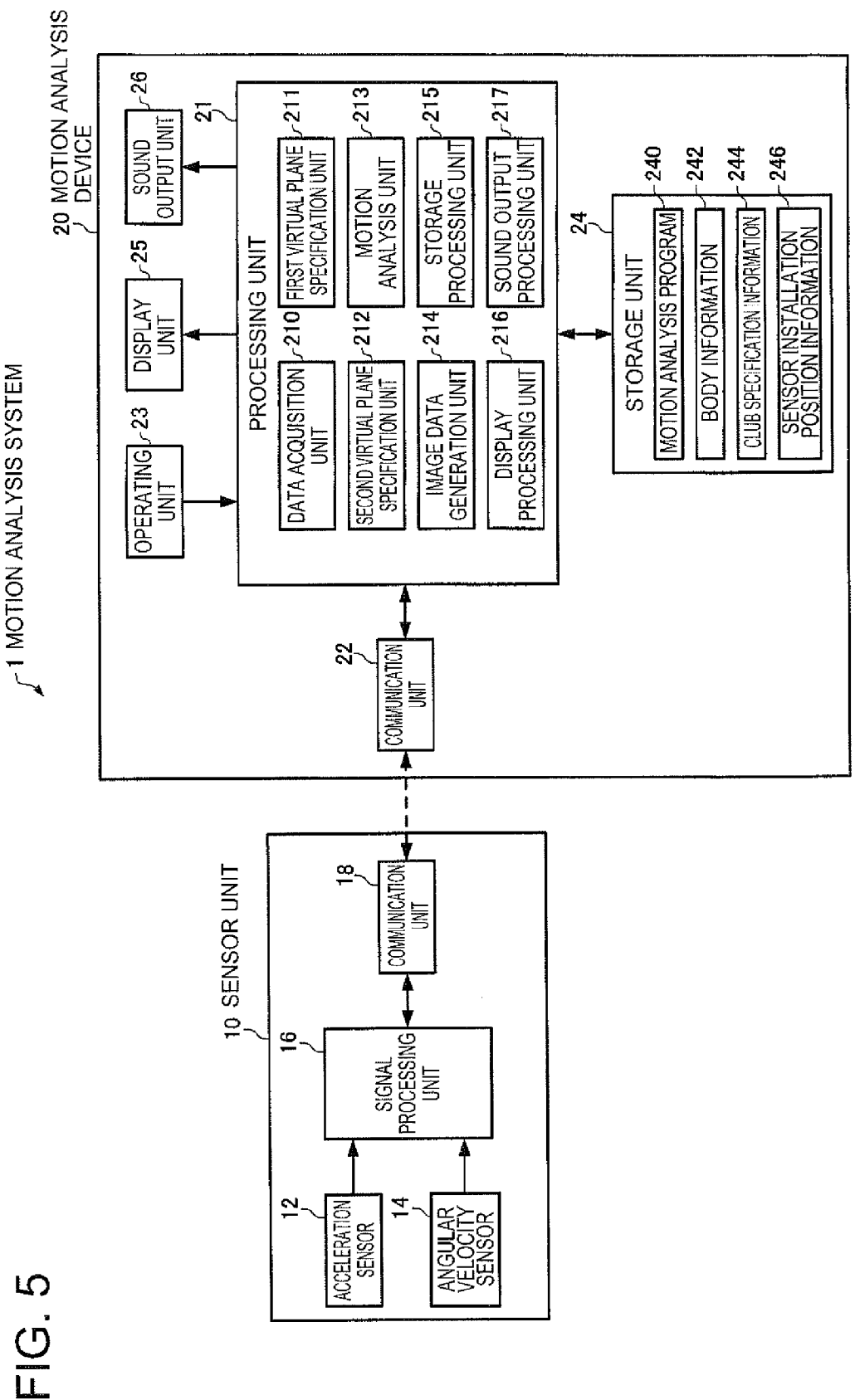
FIG. 5 is a diagram illustrating an example of the configuration of the motion analysis system according to the embodiment.

FIG. 5 is a diagram illustrating an example of the configuration of the sensor unit 10 and the motion analysis device 20. As illustrated in FIG. 5, in the embodiment, the sensor unit 10 includes an acceleration sensor 12, an angular velocity sensor 14, a signal processing unit 16, and a communication unit 18.

The acceleration sensor 12 measures acceleration which is generated in each of the 3 axial directions which intersect with each other (ideally, cross at right angles), and outputs a digital signal (acceleration data) according to the magnitude and orientation of each of the measured 3 axial accelerations.

The angular velocity sensor 14 measures angular velocity which is generated around each of the 3 axes which intersect with each other (ideally, cross at right angles), and outputs a digital signal (angular velocity data) according to the magnitude and orientation of each of the measured 3 axial angular velocities.

The signal processing unit 16 receives the acceleration data and the angular velocity data from the acceleration sensor 12 and the angular velocity sensor 14, respectively, stores the acceleration data and the angular velocity data in a storage unit, which is not shown in the drawing, after attaching time information to the acceleration data and the angular velocity data, generates packet data, which is adjusted to a format for communication, by attaching time information to the stored measurement data (the acceleration data and the angular velocity data), and outputs the packet data to the communication unit 18.

Although it is ideal that the acceleration sensor 12 and the angular velocity sensor 14 are attached to the sensor unit 10 such that the respective 3 axes match the 3 axes (the x axis, the y axis, and the z axis) of the orthogonal coordinate system (sensor coordinate system) which is defined for the sensor unit 10, an attachment angular error occurs in reality. Here, the signal processing unit 16 performs a process of converting the acceleration data and the angular velocity data into data of the xyz coordinate system using a correction parameter which is calculated in advance according to the attachment angular error.

Further, the signal processing unit 16 may perform a process of correcting the temperature of the acceleration sensor 12 and the angular velocity sensor 14. Otherwise, a function of correcting temperature may be embedded in the acceleration sensor 12 and the angular velocity sensor 14.

Meanwhile, the acceleration sensor 12 and the angular velocity sensor 14 may output an analog signal. In this case, the signal processing unit 16 may generate the measurement data (the acceleration data and the angular velocity data) by performing A/D conversion on the output signal of the acceleration sensor 12 and the output signal of the angular velocity sensor 14, respectively, and may generate the packet data for communication using the measurement data.

The communication unit 18 performs a process of transmitting the packet data, which is received from the signal processing unit 16, to the motion analysis device 20, or a process of receiving a control command from the motion analysis device 20 and transmitting the control command to the signal processing unit 16. The signal processing unit 16 performs various processes according to the control command.

The motion analysis device 20 includes a processing unit 21, a communication unit 22, an operating unit 23, a storage unit 24, a display unit 25, and a sound output unit 26.

The communication unit 22 performs a process of receiving the packet data from the sensor unit 10 and transmitting the packet data to the processing unit 21, or a process of transmitting the control command, which is received from the processing unit 21, to the sensor unit 10.

The operating unit 23 performs a process of acquiring operating data from the user and transmitting the operating data to the processing unit 21. The operating unit 23 may include, for example, a touch panel type display, buttons, keys, or a microphone.

The storage unit 24 includes, for example, various IC memories, such as a Read Only Memory (ROM), a flash ROM, and a Random Access Memory (RAM), or a recording medium such as a hard disk or a memory card.

The storage unit 24 stores programs which are used to perform various calculation processes and control processes by the processing unit 21, various programs and data which are used to realize application functions, or the like. More specifically, in the embodiment, the storage unit 24 stores a motion analysis program 240 which is read by the processing unit 21 and which is used to execute a motion analysis process. The motion analysis program 240 may be stored in a nonvolatile recording medium in advance or the motion analysis program 240 may be received by the processing unit 21 from a server through a network and stored in the storage unit 24.

In addition, in the embodiment, the storage unit 24 stores the body information 242 of the user 2, club specification information 244 indicative of the specifications of the golf club 3, and sensor installation position information 246. For example, the user 2 operates the operating unit 23 and inputs the body information, such as height, weight and sex, and the input body information is stored in the storage unit 24 as the body information 242. In addition, for example, the user 2 operates the operating unit 23 and inputs the model number of a golf club 3 which is used (or selects the model number from the model number list), and sets the specification information corresponding to the input model number to the club specification information 244 from among specification information (for example, information about the length, the central position, the lie angle, the facial angle, and the loft angle of the shaft) for each model number which is stored in the storage unit 24 in advance. In addition, for example, the user 2 operates the operating unit 23 and inputs the distance between the installation position of the sensor unit 10 and the grip end of the golf club 3, and information of the input distance is stored in the storage unit as the sensor installation position information 246. Otherwise, the sensor unit 10 is mounted on a determined prescribed position (for example, a distance of 20 cm from the grip end), and the information of the prescribed position may be stored in advance as the sensor installation position information 246.

In addition, the storage unit 24 is used as the work space of the processing unit 21, and temporarily stores the data which is input from the operating unit 23, the results of operations which are executed by the processing unit 21 according to the various programs. Further, the storage unit 24 may store data, which needs to be preserved for a long time, from among data generated through processes performed by the processing unit 21.

The display unit 25 displays the results of the processes performed by the processing unit 21 as letters, graphs, tables, animation, and the other images. The display unit 25 may include, for example, a CRT, an LCD, a touch panel type display, a Head Mount Display (HMD), and the like. Meanwhile, the functions of the operating unit 23 and the display unit 25 may be realized using a single touch panel type display.

The sound output unit 26 outputs the results of processes which are performed by the processing unit 21 as sounds such as a voice or a buzzing sound. The sound output unit 26 may include, for example, a speaker, a buzzer, or the like.

The processing unit 21 performs a process of transmitting a control command to the sensor unit 10, various calculation processes for data which is received from the sensor unit 10 through the communication unit 22, and the other various control processes according to the various programs. More specifically, in the embodiment, the processing unit 21 executes the motion analysis program 240, and functions as a data acquisition unit 210, a first virtual plane specification unit 211, a second virtual plane specification unit 212, a motion analysis unit 213, an image data generation unit 214, a storage processing unit 215, a display processing unit 216, and a sound output processing unit 217.

The data acquisition unit 210 performs a process of receiving the packet data which is received by the communication unit 22 from the sensor unit 10, acquiring the time information and the measurement data from the received packet data, and transmitting the time information and the measurement data to the storage processing unit 215.

The storage processing unit 215 performs a process of receiving the time information and the measurement data from the data acquisition unit 210 and storing the time information and the measurement data in the storage unit 24 after associating the time information and the measurement data.

The first virtual plane specification unit 211 (an example of a first specification unit) performs a process of specifying the first line segment 51 along the longitudinal direction of the shaft of the golf club 3, acquired when the user is at a standstill, using the measurement data which is output by the sensor unit 10. Further, the first virtual plane specification unit 211 performs a process of specifying the shaft plane (first virtual plane) 30 (refer to FIG. 4) which includes the first line segment 51 and the third line segment 52 indicative of the target ball-hitting direction.

The first virtual plane specification unit 211 may calculate the coordinates of the position 62 of the grip end of the golf club 3 using the measurement data which is output by the sensor unit 10, and may specify the first line segment 51 using the coordinates of the position 62 of the grip end. For example, the first virtual plane specification unit 211 may calculate an angle of inclination of the shaft of the golf club 3 (inclination for the horizontal plane (XY plane) or the vertical surface (XZ plane)) using the acceleration data measured by the acceleration sensor 12 when the user 2 is at a standstill (at address), and may specify the first line segment 51 using the calculated angle of inclination and information of the length of the shaft which is included in the club specification information 244.

In addition, the first virtual plane specification unit 211 may calculate the width of the shaft plane 30 using the length of the first line segment 51 and the length of the arm of the user 2 based on the body information 242.

The second virtual plane specification unit 212 (an example of a second specification unit) performs a process of estimating the prescribed position 63 between the head and the chest of the user 2 (for example, on the line segment which connects the both shoulders) when the user 2 is at a standstill using the measurement data, which is output by the sensor unit 10, and the body information 242, and of specifying the second line segment 53 which connects the estimated prescribed position 63 to the position 62 of the head (hitting part) of the golf club 3. Further, the second virtual plane specification unit 212 performs a process of specifying the hogan plane (second virtual plane) 40 (refer to FIG. 4) which includes the second line segment 53 and the third line segment 52.

The second virtual plane specification unit 212 may estimate the prescribed position 63 using the coordinates of the position 62 of the grip end, which is calculated by the first virtual plane specification unit 211, and the length of the arm of the user 2 based on the body information 242. Otherwise, the second virtual plane specification unit 212 may calculate the coordinates of the position 62 of the grip end of the golf club 3 using the measurement data which is output by the sensor unit 10. In this case, the first virtual plane specification unit 211 may specify the shaft plane 30 using the coordinates of the position 62 of the grip end which are calculated by the second virtual plane specification unit 212.

In addition, the second virtual plane specification unit 212 may calculate the width of the hogan plane 40 using the length of the first line segment 51 and the length of the arm of the user 2 based on the body information 242.

The motion analysis unit 213 performs a process of analyzing the swing motion of the user 2 using the measurement data which is output by the sensor unit 10. More specifically, the motion analysis unit 213 first calculates an off-set volume, which is included in the measurement data, using the measurement data (the acceleration data and the angular velocity data) which is stored in the storage unit 24 and which is acquired when the user 2 is at a standstill (at address). Subsequently, the motion analysis unit 213 performs bias correction by subtracting the off-set volume from the measurement data, which is stored in the storage unit 24 and which is acquired after starting swing, and calculates the position and the posture of the sensor unit 10 during the swing movement of the user 2 (during the movement in step S2 of FIG. 3) using the measurement data on which the bias correction is performed.

For example, the motion analysis unit 213 calculates the position (initial position) of the sensor unit 10, which is acquired when the user 2 is at a standstill (at address), in XYZ coordinate system (global coordinate system) using the acceleration data, the club specification information 244, and the sensor installation position information 246 which are measured by the acceleration sensor 12, and calculates the change in the position from the initial position of the sensor unit 10 in time series by integrating the subsequent acceleration data thereafter. Since the user 2 performs the movement in step S1 of FIG. 3, the X coordinate of the initial position of the sensor unit 10 is 0. Further, as illustrated in FIG. 2, the y axis of the sensor unit 10 matches the longitudinal direction of the shaft of the golf club 3 and the acceleration sensor 12 measures only acceleration of gravity when the user 2 is at a standstill, and thus the motion analysis unit 213 is capable of calculating an angle of inclination (inclination for the horizontal plane (XY plane) or the vertical surface (XZ plane)) of the shaft using y-axis acceleration data. Further, the motion analysis unit 213 is capable of calculating the Y coordinate and the Z coordinate of the initial position of the sensor unit 10 using an angle of inclination of the shaft, club specification information 244 (the length of the shaft) and the sensor installation position information 246 (the distance from the grip end), and is capable of specifying the initial position of the sensor unit 10. Otherwise, the motion analysis unit 213 may calculate the coordinates of the initial position of the sensor unit 10 using the coordinate and the sensor installation position information 246 (the distance from the grip end) of the position 62 of the grip end of the golf club 3 which is calculated by the first virtual plane specification unit 211 or the second virtual plane specification unit 212.

In addition, the motion analysis unit 213 calculates the posture (initial posture) of the sensor unit 10, which is acquired when the user 2 is at a standstill (at address), in the XYZ coordinate system (global coordinate system) using the acceleration data which is measured by the acceleration sensor 12, and calculates the change in the posture from the initial posture of the sensor unit 10 in time series by performing a rotating operation using the angular velocity data which is subsequently measured by the angular velocity sensor 14. It is possible to realize the posture of the sensor unit 10 using, for example, a rotation angle (a roll angle, a pitch angle, or a yaw angle), an Eulerian angle, Quaternion, or the like around the X axis, the Y axis, and the Z axis. When the user 2 is at a standstill, the acceleration sensor 12 measures only the acceleration of gravity. Therefore, the motion analysis unit 213 is capable of specifying an angle which is made by each of the x axis, the y axis, and the z axis of the sensor unit 10 and the gravity direction using the 3 axial acceleration data. Further, since the user 2 performs the movement in step S1 of FIG. 3, the y axis of the sensor unit 10 is on the YZ plane when the user 2 is at a standstill, and thus the motion analysis unit 213 is capable of specifying the initial posture of the sensor unit 10.

Meanwhile, the signal processing unit 16 of the sensor unit 10 may calculate the off-set volume of the measurement data, and may perform the bias correction of the measurement data. Further, a bias correction function may be embedded in the acceleration sensor 12 and the angular velocity sensor 14. In this case, the bias correction of the measurement data, which is performed by the motion analysis unit 213, is not necessary.

In addition, the motion analysis unit 213 defines a motion analysis model (double pendulum model or the like) by taking the body information 242 (the height of the user 2 (the length of an arm)), the club specification information 244 (the length and the central position of the shaft), the sensor installation position information 246 (the distance from the grip end), the feature of the golf club 3 (rigid body or the like), the feature of the human body (a direction in which a joint bends is determined or the like), and the like into consideration, and calculates the locus of the golf club 3 when the user 2 performs swing using the motion analysis model, the position of the sensor unit 10, and information of the posture.

In addition, the motion analysis unit 213 detects timing (impact timing) at which a ball is hit during a period of the swing movement of the user 2 using the time information and the measurement data which are stored in the storage unit 24. For example, the motion analysis unit 213 calculates a composition value of the measurement data (the acceleration data and the angular velocity data) which is output by the sensor unit 10, and specifies the timing (time) at which the user 2 hits a ball based on the composition value.

In addition, the motion analysis unit 213 determines whether or not the locus of the golf club 3, acquired when swing (more specifically, down swing from when the golf club 3 is at a top position to when the golf club 3 hits (impact) a ball) is performed, is included in the space (V zone) between the shaft plane 30 and the hogan plane 40, and generates evaluation information of the swing, which is performed by the user 2, based on the result of determination.

Further, the motion analysis unit 213 generates information, such as swing rhythm from back swing to follow-through, head speed, incident angle (club pass) when hitting a ball, face angle, shaft rotation (the amount of change in the face angle during the swing), and the deceleration of the golf club 3 using the motion analysis model, the position of the sensor unit 10, and the information of the posture. Otherwise, the motion analysis unit 213 generates information of the deviation of each of the information when the user 2 performs swing a plurality of times.

The image data generation unit 214 performs a process of generating image data corresponding to the image of a result of the motion analysis, which is displayed on the display unit 25. More specifically, in the embodiment, the image data generation unit 214 generates the image data that includes the shaft plane 30 which is specified by the first virtual plane specification unit 211, the hogan plane 40 which is specified by the second virtual plane specification unit 212, and the locus of the golf club 3 which is calculated by the motion analysis unit 213 when the user 2 performs swing (more specifically, down swing). For example, the image data generation unit 214 generates the polygon data of the shaft plane 30 in which T1, T2, S1, and S2 are set to 4 apexes based on information of the respective coordinates of T1, T2, S1, and S2 illustrated in FIG. 4, and generates the polygon data of the hogan plane 40 in which T1, T2, H1, and H2 are set to 4 apexes based on information of the respective coordinates of T1, T2, H1, and H2. In addition, the image data generation unit 214 generates curve data indicative of the locus of the golf club 3 when the user 2 performs down swing. Further, the image data generation unit 214 generates image data which includes the polygon data of the shaft plane 30, the polygon data of the hogan plane 40, and the curve data indicative of the locus of the golf club 3.

The storage processing unit 215 performs a process of reading and writing the various programs or the various data for the storage unit 24. The storage processing unit 215 performs a process of associating the time information with the measurement data, which are received from the data acquisition unit 210, and storing the resulting data in the storage unit 24, and performs a process of storing the various information, which is calculated by the first virtual plane specification unit 211, the second virtual plane specification unit 212, and the motion analysis unit 213, in the storage unit 24.

The display processing unit 216 performs a process of displaying various images (which include letters and symbols in addition to the images corresponding to the image data which is generated by the image data generation unit 214) on the display unit 25. For example, after the swing motion of the user 2 ends, the display processing unit 216 displays the image corresponding to the image data, which is generated by the image data generation unit 214 on the display unit 25 automatically or according to the input operation performed by the user 2. Otherwise, the sensor unit 10 may be provided with the display unit, and the display processing unit 216 may transmit the image data to the sensor unit 10 through the communication unit 22, and may display various images on the display unit of the sensor unit 10.

The sound output processing unit 217 performs a process of outputting various sounds (which include voice, a buzzing sound, and the like) to the sound output unit 26. For example, after the swing motion of the user 2 ends, the sound output processing unit 217 may read the various information, stored in the storage unit 24, and output sounds and voice for motion analysis to the sound output unit 26, automatically or when a prescribed input operation is performed. Otherwise, the sound output unit may be provided in the sensor unit 10, and the sound output processing unit 217 may transmit the various sound data or voice data to the sensor unit 10 through the communication unit 22, and may output the various sounds or voices to the sound output unit of the sensor unit 10.

Meanwhile, an oscillation mechanism may be provided in the motion analysis device 20 or the sensor unit 10, and various information may be converted into oscillation information and presented to the user 2 by the oscillation mechanism.

1-3. Process of Motion Analysis Device

Motion Analysis Process

Figure 6:
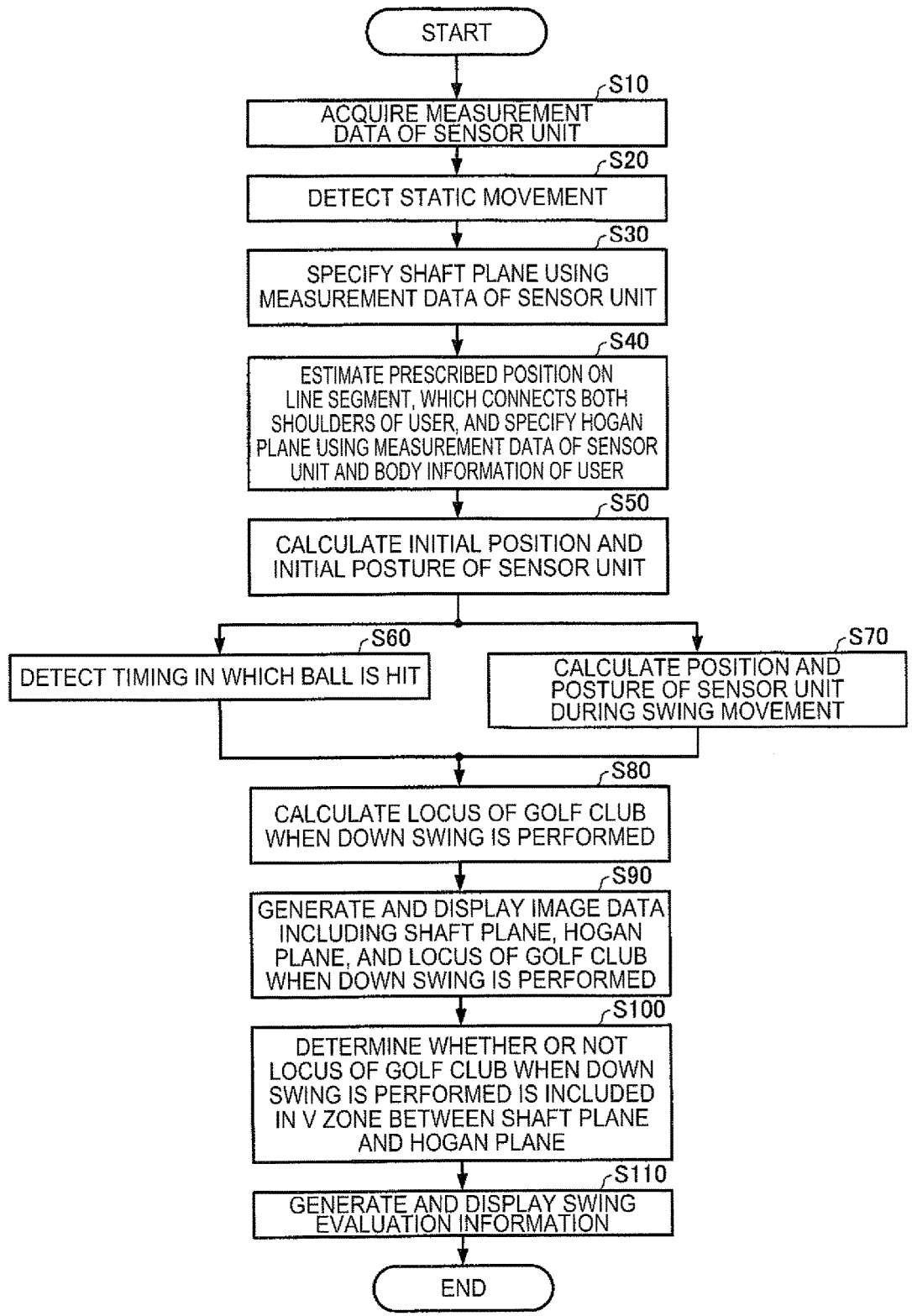
FIG. 6 is a flowchart illustrating an example of the sequence of a motion analysis process in the embodiment.

FIG. 6 is a flowchart illustrating a part of the sequence of the motion analysis process performed by the processing unit 21 in the embodiment. The processing unit 21 performs apart of the sequence of the motion analysis process according to the sequence of the flowchart of FIG. 6 by executing the motion analysis program 240, which is stored in the storage unit 24. Hereinafter, the flowchart of FIG. 6 will be described.

First, the processing unit 21 acquires the measurement data of the sensor unit 10 (S10). When the processing unit 21 acquires initial measurement data in the swing motion (including static movement) of the user 2 in step S10, the processing unit 21 may perform processes subsequent to step S20 in real time, or may perform the processes subsequent to step S20 after acquiring a part or entirety of a series of measurement data in the swing motion of the user 2 from the sensor unit 10.

Subsequently, the processing unit 21 detects the static movement (address movement) of the user 2 (movement in step S1 of FIG. 3) using the measurement data which is acquired from the sensor unit 10 (S20). When the processes are performed in real time and the processing unit 21 detects the static movement (address movement), for example, a prescribed image or a sound is output. Otherwise, an LED is provided in the sensor unit 10, the user 2 is notified about the detection of the static state by lighting the LED, and thus the user 2 may start swing after checking the notification.

Subsequently, the processing unit 21 specifies the shaft plane 30 (first virtual plane) using the measurement data, which is acquired from the sensor unit 10 (the measurement data in static movement (address movement) of the user 2), and the club specification information 244 (S30).

Subsequently, the processing unit 21 specifies the hogan plane 40 (second virtual plane) using the measurement data, which is acquired from the sensor unit 10 (the measurement data in the static movement (address movement) of the user 2), and the body information 242 (S40).

Subsequently, the processing unit 21 calculates the initial position and the initial posture of the sensor unit 10 using the measurement data, which is acquired from the sensor unit 10 (the measurement data in the static movement (address movement) of the user 2) (S50).

Subsequently, the processing unit 21 detects the timing (impact timing) at which the user 2 hits a ball using the measurement data which is acquired from the sensor unit 10 (S60).

In addition, the processing unit 21 calculates the position and the posture of the sensor unit 10 during the swing movement of the user 2 (S70) together with the process performed in step S60.

Subsequently, the processing unit 21 calculates the locus of the golf club 3 when down swing is performed by the user 2 using the impact timing detected in step S60 and the position and the posture of the sensor unit 10 calculated in step S70 (S80).

Subsequently, the processing unit 21 generates the image data including the shaft plane 30 which is specified in step S30, the hogan plane 40 which is specified in step S40, and the locus of the golf club which is calculated when down swing is performed in step S80, and displays the image data on the display unit 25 (S90).

In addition, the processing unit 21 determines whether or not the locus of the golf club 3, which is acquired when down swing is performed, is included in the V zone which is the space between the shaft plane 30 and the hogan plane 40 (S100).

Further, the processing unit 21 generates swing evaluation information of the user 2 using the result of determination in step S100, displays the swing evaluation information of the user 2 on the display unit 25 (S110), and ends the process.

Meanwhile, in the flowchart of FIG. 6, the orders of the respective steps may be appropriately changed in a possible range.

Process of Specifying Shaft Plane (First Virtual Plane)

Figure 7:
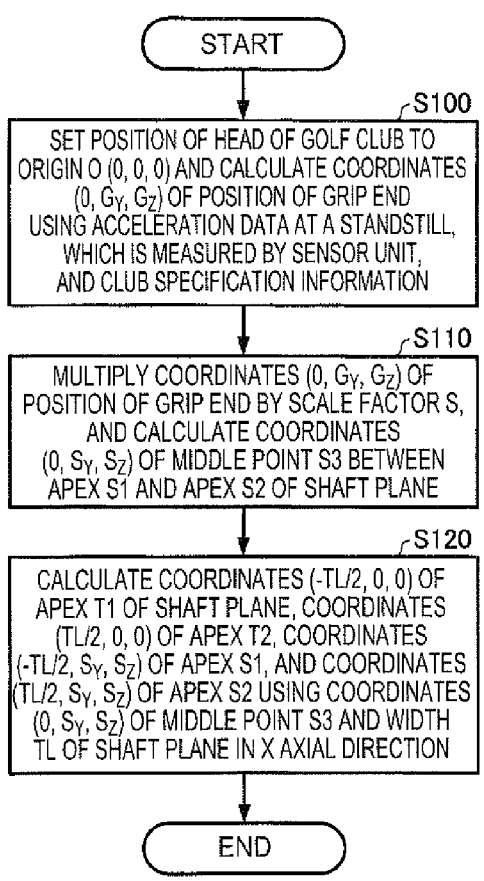
FIG. 7 is a flowchart illustrating an example of the sequence of a process of specifying the shaft plane.

FIG. 7 is a flowchart illustrating an example of the sequence of the process (the process in step S30 of FIG. 6) of specifying the shaft plane (first virtual plane) by the processing unit 21 according to the embodiment. Hereinafter, the flowchart of FIG. 7 will be described.

Figure 8:
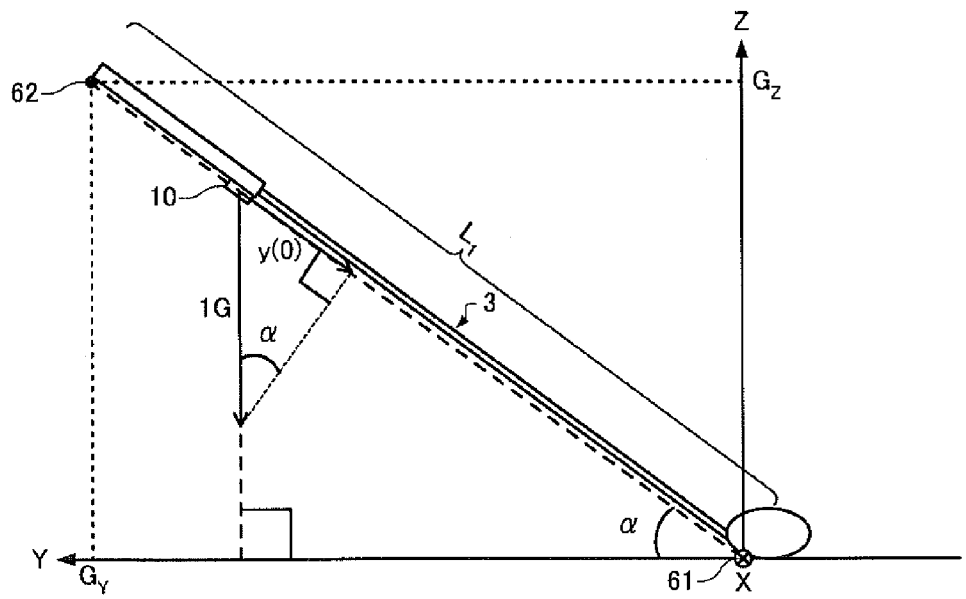
FIG. 8 is a plane view illustrating a golf club and a sensor unit which are viewed from the negative side of an X axis when the user is at a standstill.

First, as illustrated in FIG. 4, the processing unit 21 sets the position 61 of the head of the golf club 3 to the origin O (0, 0, 0) of the XYZ coordinate system (global coordinate system), and calculates the coordinates (0, $G_Y$, $G_Z$) of the position 62 of the grip end using the acceleration data at a standstill, which is measured by the sensor unit 10, and the club specification information 244 (S100). FIG. 8 is a plane view illustrating the golf club 3 and the sensor unit 10 which are viewed from the negative side of the X axis when the user 2 is at a standstill (at address). The position 61 of the head of the golf club 3 is the origin O (0, 0, 0), and the coordinates of the position 62 of the grip end are (0, $G_Y$, $G_Z$). As illustrated in FIG. 8, since the acceleration of gravity G is applied to the sensor unit 10 when the user 2 is at a standstill, the relationship between a y-axial acceleration y(0) and an angle of inclination a of the shaft of the golf club 3 (an angle made by the longitudinal axis of the shaft and the horizontal plane (XY plane)) is expressed in Equation 1.

$$y(0) = G \cdot \sin \alpha \quad (1)$$

Accordingly, when the length of the shaft of the golf club 3, which is included in the club specification information 244, is $L_1$, $G_Y$ and $G_Z$ are respectively calculated using the length of the shaft $L_1$ and the angle of inclination a, as expressed in Equations 2 and 3.

$$G_Y = L_1 \cdot \cos \alpha \quad (2)$$

$$G_Z = L_1 \cdot \sin \alpha \quad (3)$$

Subsequently, the processing unit 21 multiplies the coordinates (0, $G_Y$, $G_Z$) of the position 62 of the grip end of the golf club 3 by a scale factor S, and calculates the coordinates (0, $S_Y$, $S_Z$) of the middle point S3 between the apex S1 and the apex S2 of the shaft plane 30 (S110). That is, $S_Y$ and $S_Z$ are calculated using Equations 4 and 5.

$$S_Y = G_Y \cdot S \quad (4)$$

$$S_Z = G_Z \cdot S \quad (5)$$

Figure 9:
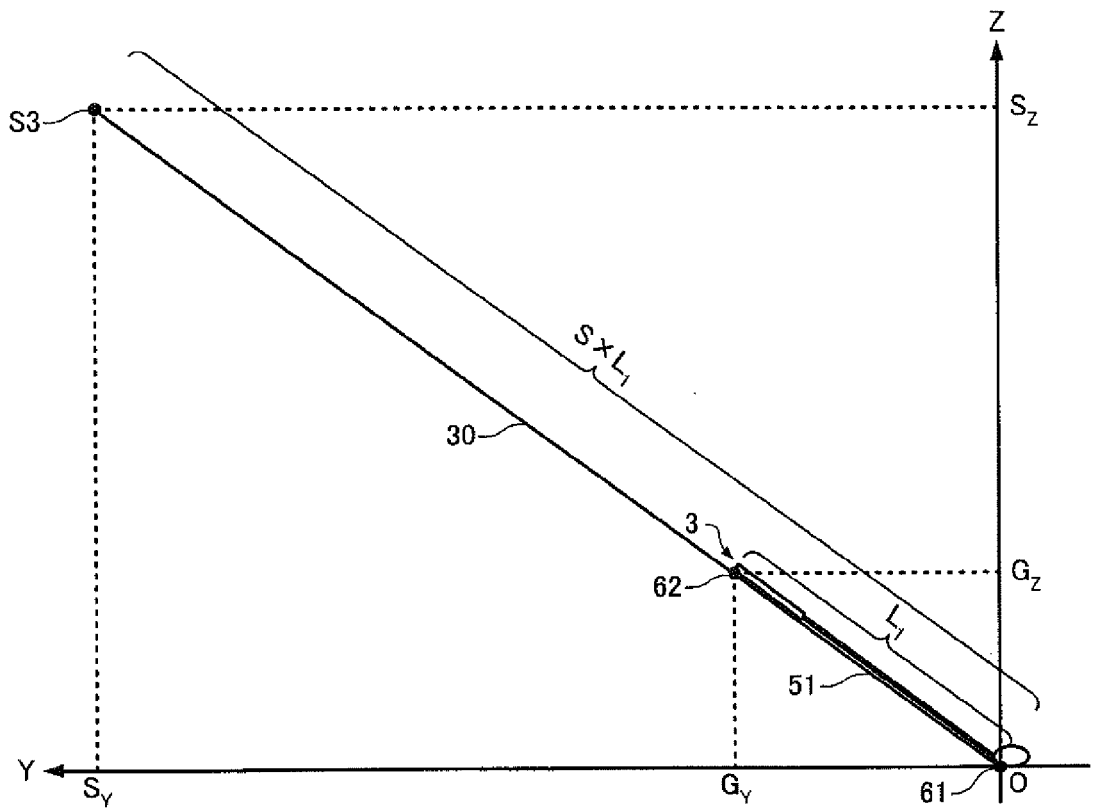
FIG. 9 is a diagram illustrating a sectional view, in which the shaft plane is cut by the YZ plane, which is viewed from the negative side of the X axis.

FIG. 9 is a diagram illustrating a sectional view, in which the shaft plane 30 of FIG. 4 is cut by the YZ plane, which is viewed from the negative side of the X axis. As illustrated in FIG. 9, the length of the line segment (the width of the direction which is perpendicular to the X axis of the shaft plane 30) which connects the middle point S3 between the apex S1 and the apex S2 to the origin O, is S times as large as the length $L_1$ of the first line segment 51. The scale factor S is set to a value which causes the locus of the golf club 3 during the swing movement of the user 2 to fall into the shaft plane 30. For example, when the length of the arm of the user 2 is set to $L_2$, the scale factor S may be set as in Equation 6 such that a width $S \times L_1$ in the direction which is perpendicular to the x axis of the shaft plane 30 is two times as large as the sum of the length $L_1$ of the shaft and the length $L_2$ of the arm.

$$S = \frac{2 \cdot (L_1 + L_2)}{L_1} \quad (6)$$

In addition, the length $L_2$ of the arm of the user 2 is related to the height $L_0$ of the user 2. For example, correlation equation such as Equation 7 is expressed when the user 2 is male, and correlation equation such as Equation 8 is expressed when the user 2 is female based on statistical information.

$$L_2 = 0.41 \times L_0 - 45.5 \text{ [mm]} \quad (7)$$

$$L_2 = 0.46 \times L_0 - 126.9 \text{ [mm]} \quad (8)$$

Accordingly, the length $L_2$ of the arm of the user is calculated using Equation 7 or 8 using the height $L_0$ of the user 2 and the sex of the user which are included in the body information 242.

Subsequently, the processing unit 21 calculates the coordinates (−TL/2, 0, 0) of the apex T1 of the shaft plane 30, the coordinates (TL/2, 0, 0) of the apex T2, the coordinates (−TL/2, S$_Y$, S$_Z$) of the apex S1, and the coordinates (TL/2, S$_Y$, S$_Z$) of the apex S2 using the coordinates (0, S$_Y$, S$_Z$) of the middle point S3, which are calculated in step S110, and the width (the length of the third line segment 52) TL of the shaft plane 30 in the X axial direction (S120). The width TL of the X axial direction is set to a value which causes the locus of the golf club 3 during the swing movement of the user 2 to fall into the shaft plane 30. For example, the width TL of the X axial direction may be set similarly to a width S×L$_1$ in the direction which is perpendicular to the X axis, that is, the width TL in the X axial direction may be set to be two times as large as the sum of the length L$_1$ of the shaft and the length L$_2$ of an arm.

The shaft plane 30 is specified using the coordinates of the 4 apexes T1, T2, S1, and S2 which are calculated as described above.

Process of Specifying Hogan Plane (Second Virtual Plane)

Figure 10:
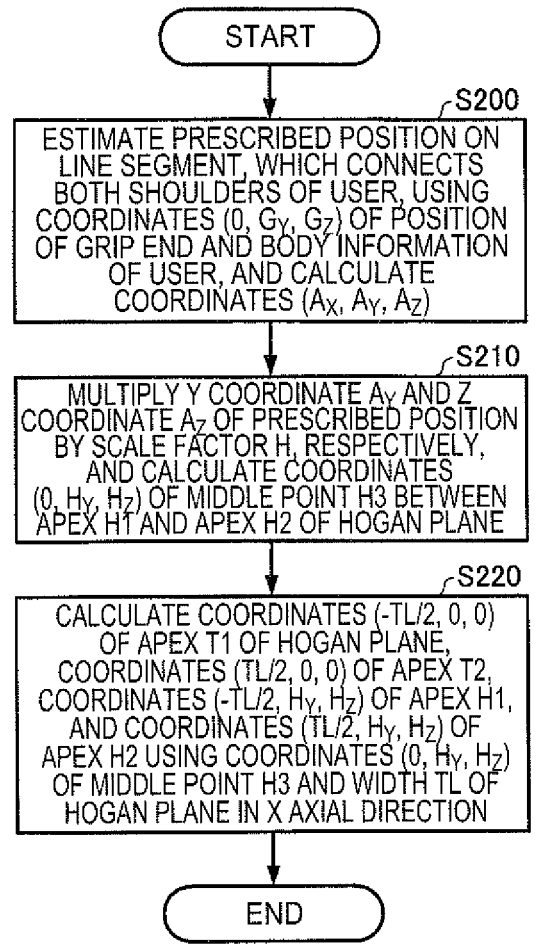
FIG. 10 is a flowchart illustrating an example of the sequence of a process of specifying the hogan plane.

FIG. 10 is a flowchart illustrating an example of the sequence of the process (the process in step S40 of FIG. 6) of specifying the hogan plane (second virtual plane) by the processing unit 21 according to the embodiment. Hereinafter, the flowchart of FIG. 10 will be described.

First, the processing unit 21 estimates the prescribed position 63 on the line segment which connects the both shoulders of the user 2, using the coordinates (0, G$_Y$, G$_Z$) of the position 62 of the grip end of the golf club 3, which is calculated in step S100 of the FIG. 7, and the body information 242 of the user 2, and calculates coordinates (A$_X$, A$_Y$, A$_Z$) (S200).

Figure 11:
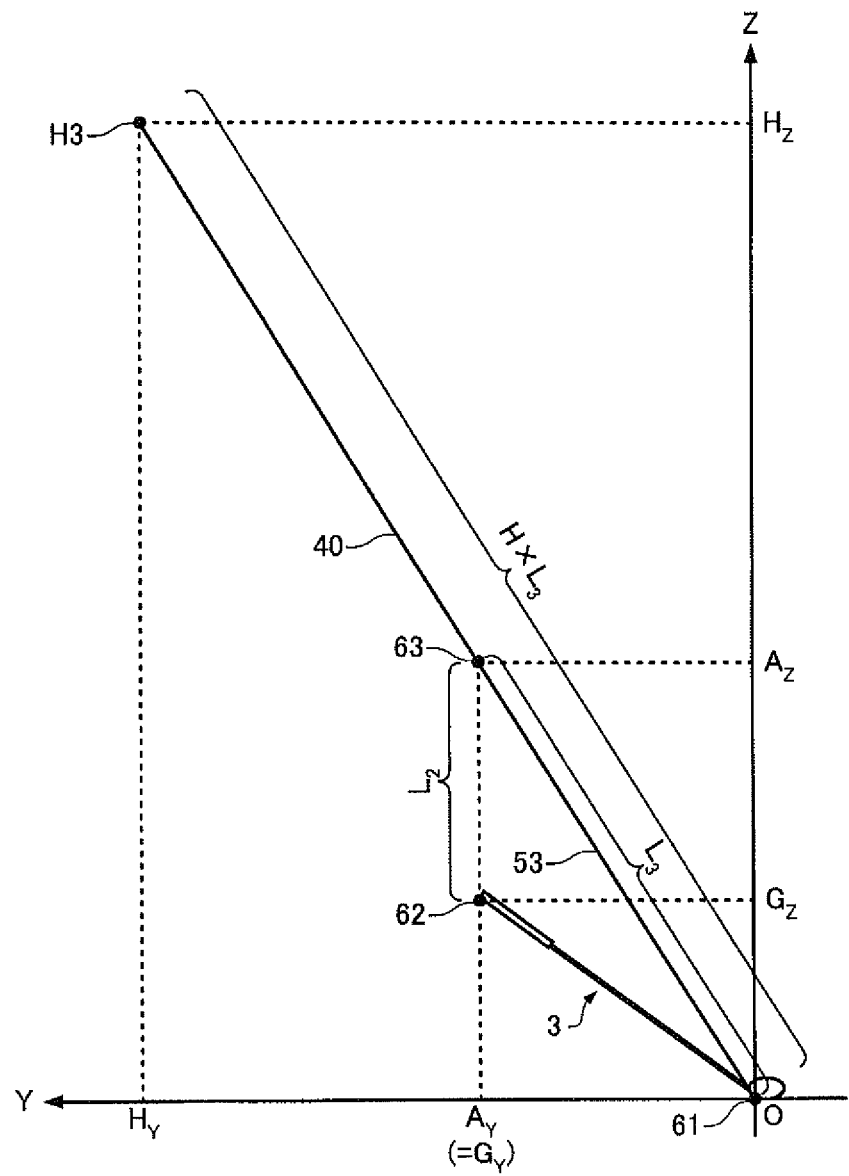
FIG. 11 is a diagram illustrating a sectional view, in which the hogan plane is cut by the YZ plane, which is viewed from the negative side of the X axis.

FIG. 11 is a diagram illustrating a sectional view, in which the hogan plane 40 of FIG. 4 is cut by the YZ plane, which is viewed from the negative side of the X axis. In FIG. 11, the middle point of the line segment which connects the both shoulders of the user 2 is set to the prescribed position 63, and the prescribed position 63 is present on the YZ plane. Accordingly, the X coordinate A$_X$ of the prescribed position 63 is 0. Further, as illustrated in FIG. 11, the processing unit 21 estimates that a position, which is acquired by moving the position 62 of the grip end of the golf club 3 to the positive direction of the Z axis by the length L$_2$ of the arm of the user 2, is the prescribed position 63. Accordingly, the Y coordinate A$_Y$ of the prescribed position 63 is the same as the Y coordinate G$_Y$ of the position 62 of the grip end, and the Z coordinate A$_Z$ of the prescribed position 63 is calculated as the sum of the Z coordinate G$_Z$ of the position 62 of the grip end and the length L$_2$ of the arm of the user 2 as in Equation 9.

$$A_Z = G_Z + L_2 \quad (9)$$

The length L$_2$ of an arm of the user is calculated by Equations 7 and 8 using the height L$_0$ and sex of the user 2 which are included in the body information 242.

Subsequently, the processing unit 21 multiplies the Y coordinate A$_Y$ and the Z coordinate A$_Z$ of prescribed position 63 by a scale factor H, respectively, and calculates the coordinates (0, H$_Y$, H$_Z$) of the middle point H3 between the apex H1 and the apex H2 of the hogan plane 40 (S210). That is, H$_Y$ and H$_Z$ are calculated by Equations 10 and 11.

$$H_Y = A_Y \cdot H \quad (10)$$

$$H_Z = A_Z \cdot H \quad (11)$$

As illustrated in FIG. 11, the length (the width of the hogan plane 40 in the direction which is perpendicular to the X axis) of the line segment which connects the middle point H3 between the apex H1 and the apex H2 to the origin O is H times as large as the length L$_3$ of the second line segment 53. The scale factor H is set to a value which causes the locus of the golf club 3 during the swing movement of the user 2 to fall into the hogan plane 40. For example, the hogan plane 40 may have the same shape and size as the shaft plane 30. In this case, the width H×L$_3$ of the hogan plane 40 in the direction which is perpendicular to the X axis matches the width S×L$_1$ of the shaft plane 30 in the direction which is perpendicular to the X axis, and is two times as large as the sum of the length L$_1$ of the shaft of the golf club 3 and the length L$_2$ of the arm of the user 2. Therefore, the scale factor H may be set as in Equation 12.

$$H = \frac{2 \cdot (L_1 + L_2)}{L_3} \quad (12)$$

In addition, the length L$_3$ of the second line segment 53 is calculated by Equation 13 using the Y coordinate A$_Y$ and Z coordinate A$_Z$ of the prescribed position 63.

$$L_3 = \sqrt{A_Y^2 + A_Z^2} \quad (13)$$

Subsequently, the processing unit 21 calculates the coordinates (−TL/2, 0, 0) of the apex T1 of the hogan plane 40, the coordinates (TL/2, 0, 0) of the apex T2, the coordinates (−TL/2, H$_Y$, H$_Z$) of the apex H1, and the coordinates (TL/2, H$_Y$, H$_Z$) of the H2 using the coordinates (0, H$_Y$, H$_Z$) of the middle point H3, which is calculated in step S210, and the width (the length of the third line segment 52) TL of the hogan plane 40 in the X axial direction (S220). The width TL of the X axial direction is set to a value which causes the locus of the golf club 3 during the swing movement of the user 2 to fall into the hogan plane 40. In the embodiment, the width TL of the hogan plane 40 in the X axial direction is the same as the width of the shaft plane 30 in the X axial direction, and thus, as described above, the width TL of the hogan plane 40 may be two times as large as the sum of the length L$_1$ of the shaft and the length L$_2$ of an arm.

The hogan plane 40 is specified using the coordinates of the 4 apexes T1, T2, H1, and H2 which are calculated as described above.

Process of Detecting Impact

Figure 12:
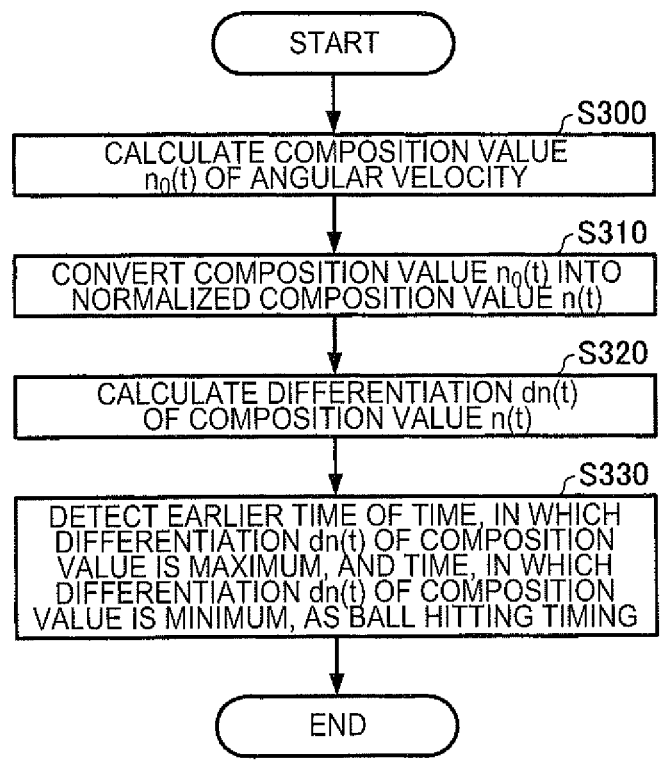
FIG. 12 is a flowchart illustrating an example of the sequence of a process of detecting timing at which the user hits a ball.

FIG. 12 is a flowchart illustrating an example of the sequence of the process (process in step S60 of FIG. 6) of detecting timing at which the user 2 hits a ball. Hereinafter, the flowchart of FIG. 12 will be described.

First, the processing unit 21 calculates the composition value n$_0$(t) of the angular velocity at each time t using the acquired angular velocity data (the angular velocity data for each time t)(S300). For example, when the angular velocity data includes x(t), y(t), and z(t) at time t, the composition value n$_0$(t) of the angular velocity is calculated as in subsequent Equation 14.

$$n_0(t) = \sqrt{x(t)^2 + y(t)^2 + z(t)^2} \quad (14)$$

Subsequently, the processing unit 21 converts the composition value n$_0$(t) of the angular velocity at each time t into a composition value n(t) which is normalized (scaled) to a prescribed range (S310). For example, when the maximum value of the composition value of the angular velocities during a period, in which the measurement data is acquired, is max ($n_0$), the composition value $n_0(t)$ of the angular velocity is converted to the composition value $n(t)$ which is normalized to a range of 0 to 100 through subsequent Equation 15.

$$n(t) = \frac{100 \times n_0(t)}{\max(n_0)} \quad (15)$$

Subsequently, the processing unit 21 calculates the differentiation dn(t) of the composition value n(t) after normalization is performed at each time t (S320). For example, when the measurement period of the 3 axial angular velocity data is $\Delta t$, the differentiation (difference) dn(t) of the composition value of the angular velocities at time t is calculated as in subsequent Equation 16.

$$dn(t)=n(t)-n(t-\Delta t) \quad (16)$$

At last, the processing unit 21 detects the earlier time of time, in which the value of the differentiation dn(t) of the composition value is the maximum, and time, in which the value of the differentiation do (t) of the composition value is the minimum, as the ball hitting timing (S330). In normal golf swing, it is considered that a swing speed is the maximum at a ball hitting moment. Further, since it may be considered that the composition value of the angular velocity changes according to the swing speed, it is possible to understand timing at which the differentiation value of the composition value of the angular velocities during a series of swing movement is the maximum or the minimum (that is, timing at which the differentiation value of the composition value of the angular velocities is the positive maximum value or the negative minimum value) as ball hitting (impacting) timing. Meanwhile, since the golf club 3 is oscillated due to the ball hitting, it is considered that timing at which the differentiation value of the composition value of the angular velocities is the maximum or the minimum occurs in pairs. However, the earlier timing thereof is considered as the ball hitting moment.

Meanwhile, when the user 2 performs the swing movement, a series of rhythms, in which the user stops the golf club at the top position, performs down swing, hits a ball, and performs follow-through, are assumed. Accordingly, the processing unit 21 detects the candidates of the timing at which the user 2 hits a ball according to the flowchart of FIG. 12, determines whether or not the measurement data, which is acquired before or after the detected timing, matches the rhythm. The detected timing may be confirmed as the timing at which the user 2 hits a ball when the measurement data matches the rhythm, and a subsequent candidate may be detected when the measurement data does not match the rhythm.

In addition, in a flowchart of FIG. 12, the processing unit 21 detects the ball hitting timing using the 3 axial angular velocity data. Meanwhile, it is possible to detect the ball hitting timing using the 3 axial acceleration data in the same manner.

Process of Calculating Posture of Sensor Unit

Figure 13:
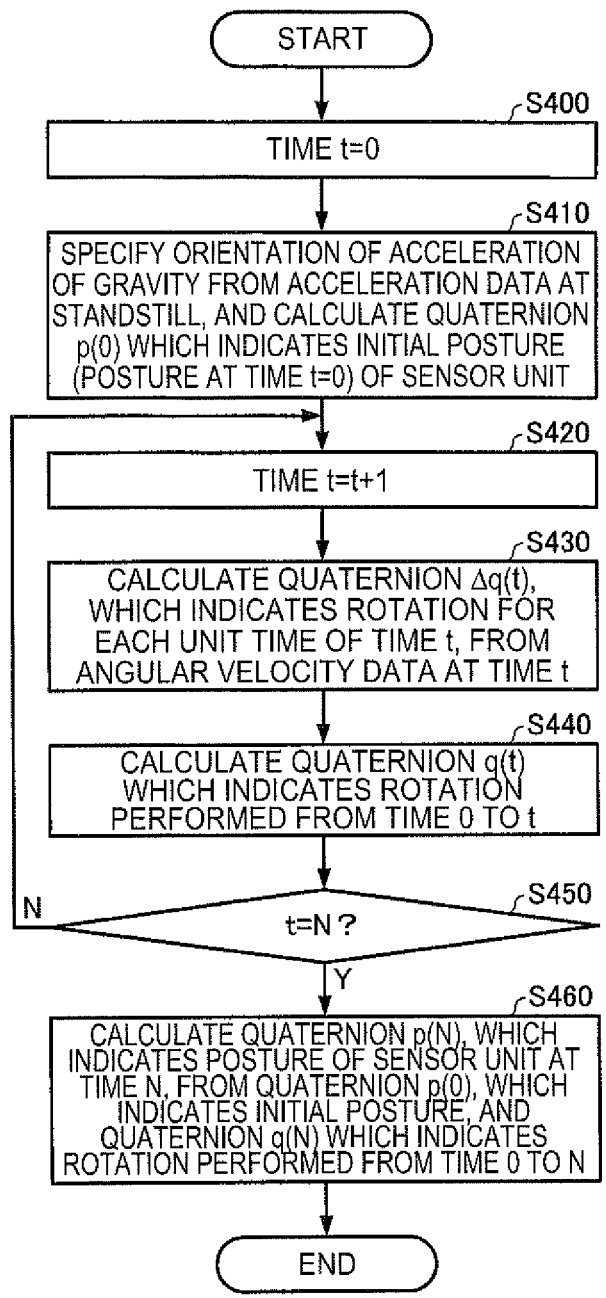
FIG. 13 is a flowchart illustrating an example of the sequence of a process of calculating the posture of the sensor unit.

FIG. 13 is a flowchart illustrating an example of the sequence of the process (some processes in step S50 and step S70 of FIG. 6) of calculating the posture of the sensor unit 10 (initial posture and posture at time N). Hereinafter, the flowchart of FIG. 13 will be described.

First, the processing unit 21 makes setting such that time t=0 (S400), specifies the orientation of the acceleration of gravity from the 3 axial acceleration data at a standstill, and calculates quaternion p(0) which indicates the initial posture (posture at time t=0) of the sensor unit 10 (S410).

For example, when the initial posture is the vector ($X_0$, $Y_0$, $Z_0$) of an arbitrary XYZ coordinate system, quaternion p(0) is expressed as in Equation 17.

$$p(0)=(0,X_0,Y_0,Z_0) \quad (17)$$

In addition, quaternion q, which indicates rotation, is expressed as in subsequent Equation 18.

$$q=(w,x,y,z) \quad (18)$$

In Equation 18, when a rotation angle of target rotation is $\varphi$ and the unit vector of the rotational axis is ($r_x$, $r_y$, $r_z$), w, x, y, and z are expressed as in subsequent Equation 19.

$$w = \cos\frac{\phi}{2},\ x = r_x \cdot \sin\frac{\phi}{2},\ y = r_y \cdot \sin\frac{\phi}{2},\ z = r_z \cdot \sin\frac{\phi}{2} \quad (19)$$

Since the sensor unit 10 stops at time t=0, $\varphi$=0. Quaternion q(0), which indicates the rotation at time t=0, is expressed as in subsequent Equation 20 using Equation 18 in which $\varphi$=0 is substituted for Equation 19.

$$q(0)=(1,0,0,0) \quad (20)$$

Subsequently, the processing unit 21 updates time t to t+1 (S420), and calculates quaternion $\Delta q(t)$, which indicates rotation for each unit time of time t, from the 3 axial angular velocity data at time t (S430).

For example, when the 3 axial angular velocity data at time t is $\omega(t)=(\omega_x(t), \omega_y(t), \omega_z(t))$, the size $|\omega(t)|$ of the angular velocity for a single sample which is measured at time t is calculated using subsequent Equation 21.

$$|\omega(t)|=\sqrt{\omega_x(t)^2+\omega_y(t)^2+\omega_z(t)^2} \quad (21)$$

Since the size $|\omega(t)|$ of the angular velocity is a rotation angle for each unit time, quaternion $\Delta q(t+1)$ which indicates rotation for each unit time of time t is calculated using subsequent Equation 22.

$$\Delta q(t) = \left(\cos\frac{|\omega(t)|}{2},\ \frac{\omega_x(t)}{|\omega(t)|}\sin\frac{|\omega(t)|}{2},\ \frac{\omega_y(t)}{|\omega(t)|}\sin\frac{|\omega(t)|}{2},\ \frac{\omega_z(t)}{|\omega(t)|}\sin\frac{|\omega(t)|}{2}\right) \quad (22)$$

Here, since t=1, the processing unit 21 calculates $\Delta q(1)$ using Equation 11 from the 3 axial angular velocity data $\omega(1)=(\omega_x(1), \omega_y(1), \omega_z(1))$ at time t=1.

Subsequently, the processing unit 21 calculates quaternion q(t) which indicates rotation performed from time 0 to t (S440). Quaternion q(t) is calculated using subsequent Equation 23.

$$q(t)=q(t-1)\cdot\Delta q(t) \quad (23)$$

Here, since t=1, the processing unit 21 calculates q(1) using Equation 23 based on q(0) of Equation 20 and $\Delta q(1)$ which is calculated in step S430.

Subsequently, the processing unit 21 repeats the processes in steps S420 to S440 until t=N. When t=N (Y in S450), the processing unit 21 calculates quaternion p(N), which indicates posture at time N, based on quaternion p(0), which indicates the initial posture calculated in step S410, and quaternion q(N), which indicates rotation performed from when time t=0 to when t=N and which is calculated in the last step S440, using subsequent Equation 24 (S460), and ends the process.

$$p(N)=q(N)\cdot p(0)\cdot q^*(N) \quad (24)$$

In Equation 24, q*(N) is the conjugating quaternion of q(N). p (N) is expressed as in subsequent Equation 25. The posture of the sensor unit 10 at time N is ($X_N$, $Y_N$, $Z_N$) when being described using the vector of the XYZ coordinate system.

$$p(N)=(0, X_N, Y_N, Z_N) \quad (25)$$

The processing unit 21 calculates the posture of the sensor unit 10 when the user hits a ball while the time that the user 2 hits a ball is set to time N.

1-4. Swing Evaluation

Figure 14:
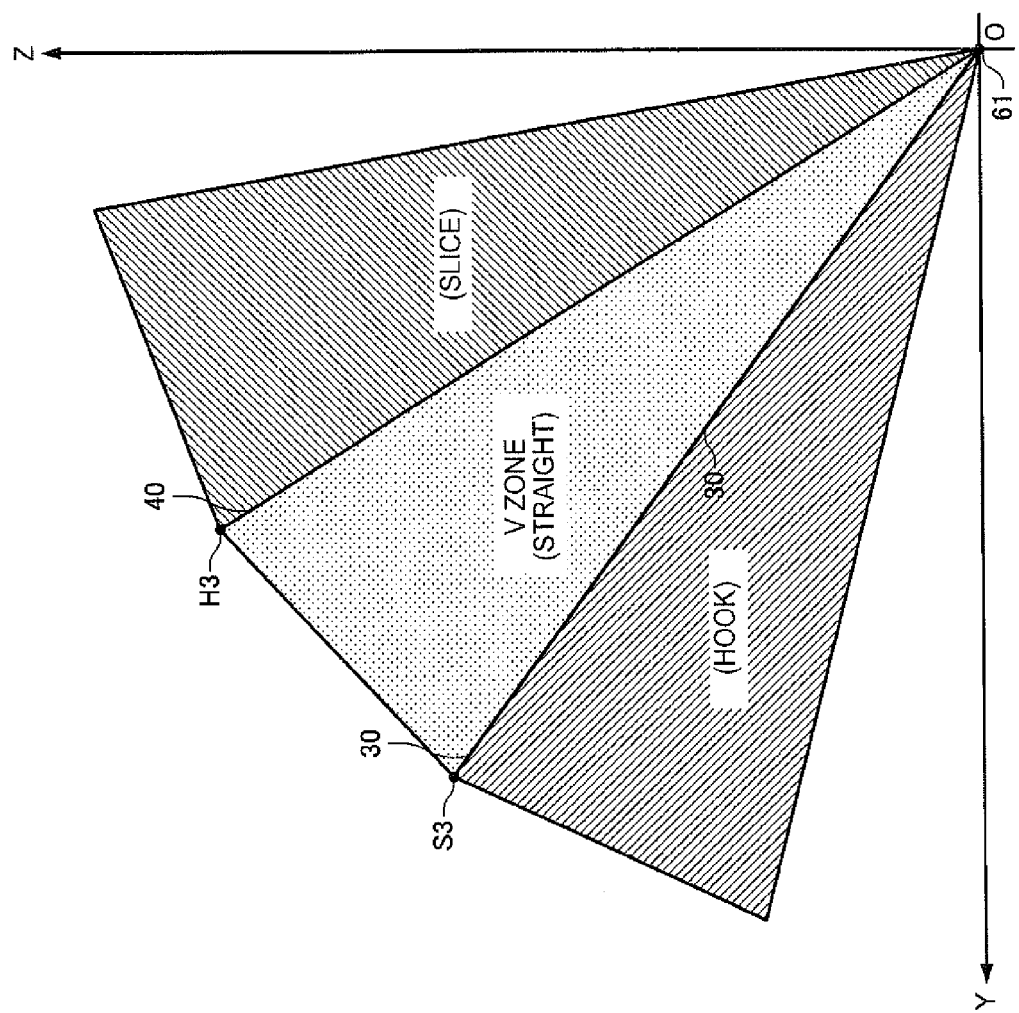
FIG. 14 is a diagram illustrating the shaft plane and the hogan plane which are viewed from the negative side of the X axis (diagram which is projected on the YZ plane).

FIG. 14 is a diagram illustrating the shaft plane 30 and the hogan plane 40 of FIG. 4, which are viewed from the negative side of the X axis (diagram which is projected on the YZ plane). As illustrated in FIG. 14, when the entire locus of the golf club 3, which is acquired when down swing is performed by the user 2, is included in the V zone which is the space between the shaft plane 30 and the hogan plane 40, there is a high possibility of a straight ball. In contrast, when the down swing is performed by the user 2 and when a part of the locus of the golf club 3 is included in the lower space than the V zone, there is a high possibility of a hook ball. When the part of the down swing is included in the higher space than the V zone, there is a high possibility of a slice ball. Here, for example, the processing unit 21 may determine whether or not the entire locus of the golf club 3, which is acquired when down swing is performed by the user 2, is included in the V zone in step S100 of FIG. 6. Further, the processing unit 21 may evaluate proper swing when the entire locus of the golf club 3, which is acquired when down swing is performed, is included in the V zone in step S110, and may evaluate improper swing of a hook or a slice when a part of the locus of the golf club 3, which is acquired when down swing is performed, is not included in the V zone. In a case of display, display may not be performed using a plane, and swing may be evaluated in such a way that only the first line segment 51 of the shaft plane 30 and the second line segment 53 of the hogan plane 40 are displayed, as illustrated in FIG. 14.

Figure 15:
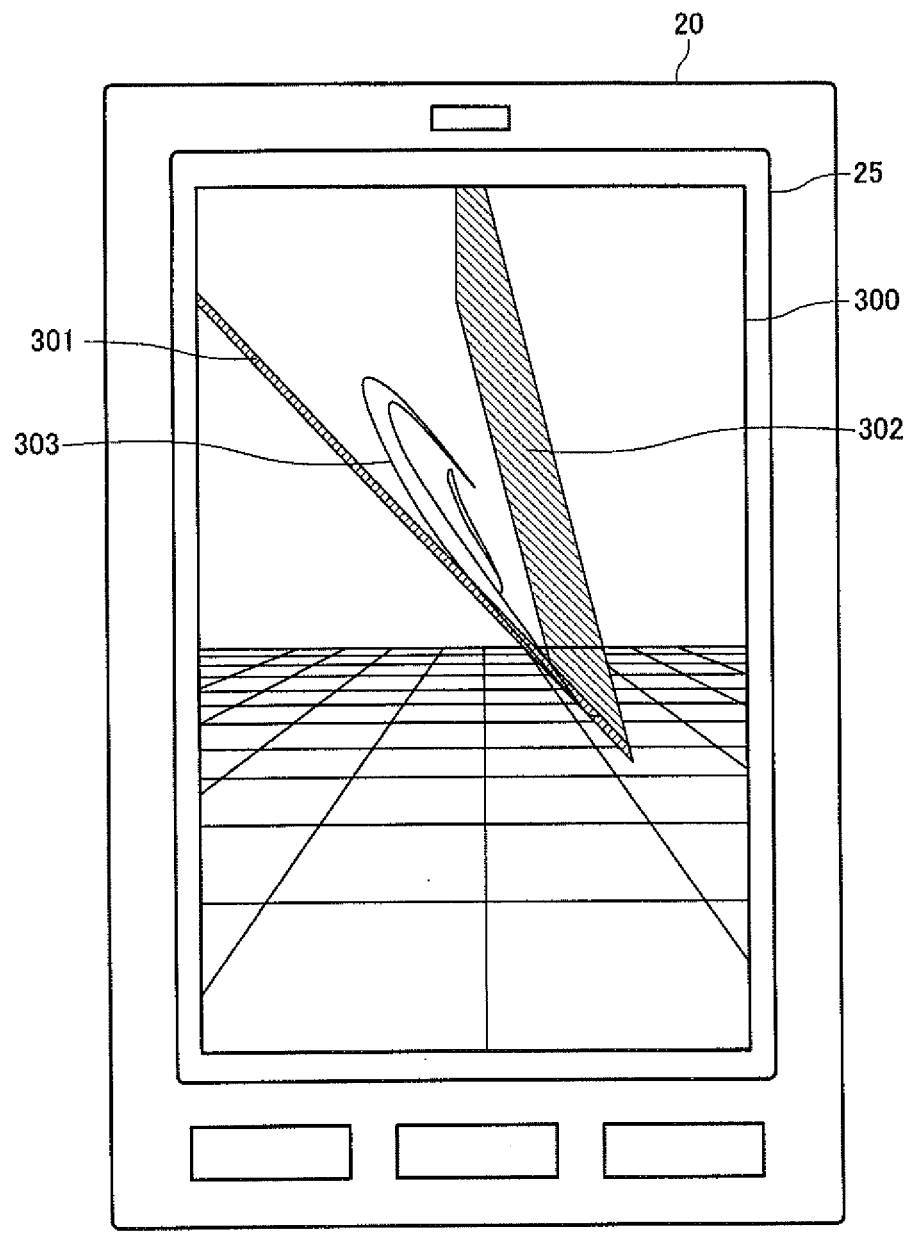
FIG. 15 is a diagram illustrating an example of an image which is displayed on a display unit.

FIG. 15 is a diagram illustrating an example of an image which is generated by the processing unit 21 in step S90 of FIG. 6 and which is displayed on the display unit 25. An image 300, which is illustrated in FIG. 15, includes a polygon 301 which indicates the shaft plane 30, a polygon 302 which indicates the hogan plane 40, and a curve 303 which indicates the locus of the golf club 3 acquired when down swing is performed by the user 2. In the image 300 illustrated in FIG. 15, the entire curve 303 is included in the V zone which is the space between the polygon 302 and the polygon 303. Accordingly, the user 2 is capable of recognizing that swing performed by the user 2 is proper by viewing the image 300. In addition, when the processing unit 21 displays the image 300 (image in which the entire curve 303 is included in the V zone) illustrated in FIG. 15 on the display unit 25, the processing unit 21 may evaluate that the user's swing is proper in step S110 of FIG. 6, and may display information of the result of the evaluation on the display unit 25 together with the image 300.

Meanwhile, the image 300 illustrated in FIG. 15 may be a still image or a moving picture. In addition, the image 300 may be a 3-dimensional image which is capable of changing a display angle (viewpoint to watch the image 300) according to an operation performed by the user 2.

1-5. Advantage

According to the embodiment, the user 2 is capable of objectively recognizing a posture at a standstill based on the positions and inclinations of the shaft plane 30 and the hogan plane 40, the size of the V zone, and the like using the image 300 which is displayed on the display unit 25 of the motion analysis device 20. In addition, the user 2 is capable of recognizing the path of the golf club 3, which is acquired when down swing is performed, and the positional relationship (whether or not the path of the golf club 3 is included in the V zone) between the shaft plane 30 and the hogan plane 40, and thus it is possible to accurately evaluate good or bad of swing, compared to the related art.

In addition, according to the embodiment, restrictions, in which the user 2 should address such that the longitudinal axis of the shaft of the golf club 3 is perpendicular to the target line, are provided, and thus the motion analysis device 20 is capable of specifying the third line segment 52, which indicates the target ball-hitting direction, using the measurement data of the sensor unit 10 at address. Accordingly, the motion analysis device 20 is capable of properly specifying the shaft plane 30 and the hogan plane 40 in accordance with the direction of the third line segment 52.

In addition, according to the embodiment, the motion analysis device 20 sets the Z coordinate $A_Z$ of the prescribed position 63 on the line segment, which connects the both shoulders of the user 2, to the sum of the Z coordinate $G_Z$ of the position 62 of the grip end on the shaft plane 30 and the length $L_2$ of the arm of the user 2, and thus it is possible to specify the shaft plane 30 and the hogan plane 40 using the measurement data of the single sensor unit 10. Accordingly, according to the embodiment, it is possible to more accurately specify the hogan plane 40 in accordance with the body shape of the user 2, compared to a case in which a virtual plane, acquired by rotating the shaft plane 30 by a prescribed angle (for example, 30°) centering on the X axis, is set to the hogan plane 40.

In addition, according to the embodiment, the motion analysis device 20 calculates the length of the arm $L_2$ from height information, which is included in the body information 242 of the user 2, using a correlation equation between the height and the length of the arm which are deduced based on the statistical data, and thus it is not necessary for the user 2 to input length information of the arm, the accurate numerical value of which is not normally known, thereby being convenient.

In addition, according to the embodiment, the shaft plane 30 and the hogan plane 40 are specified using the sensor unit 10, it is not necessary to use a large scale device, such as a camera, and thus restrictions on a place in which swing analysis is performed are small.

In addition, according to the embodiment, the motion analysis device 20 determines whether or not the locus of the golf club 3 is included in the V zone when down swing is performed, and presents the swing evaluation information based on the result of determination, and thus it is possible for the user 2 to objectively and easily evaluate good or bad of swing.

2. Modification Example

The invention is not limited to the embodiment and various modifications are possible without departing from the gist of the invention.

For example, in the embodiment, the motion analysis device 20 calculates the Z coordinate $A_Z$ of the prescribed position 63 on the line segment, which connects the both shoulders of the user 2, as the sum of the Y coordinate $G_Y$ of the position 62 of the grip end and the length $L_2$ of the arm of the user 2 as in Equation 9. However, another equation may be used. For example, the motion analysis device 20 may acquire $A_Z$, by multiplying $L_2$ by a coefficient K and adding the resulting value to $G_Y$, that is, $A_Z=G_Y+K\cdot L_2$.

In addition, in the embodiment, the motion analysis device 20 specifies the shaft plane and the hogan plane using the measurement data of the sensor unit 10 which is mounted on the golf club 3, and calculates the locus of the golf club 3 during swing. However, in addition thereto, the shaft plane and the hogan plane may be specified and the locus of the golf club 3 may be calculated using, for example, measurement data of the sensor unit 10 which is mounted on the arm (wrist or the like) of the user 2 through the same method as in the embodiment. Otherwise, a plurality of sensor units 10 are mounted on the golf club 3 or the part of the user, such as the arm or the shoulder, and the shaft plane and the hogan plane may be specified and the locus of the golf club 3 may be calculated using the measurement data of each of the plurality of sensor units 10.

In addition, in the embodiment, the sensor unit detects timing at which user 2 hits (impacts) a ball using the square root value of the sum of squares as shown in Equation 14 as the measured composition value of the 3 axial angular velocities. However, in addition thereto, for example, the sum of squares of the 3 axial angular velocities, the sum or average of the 3 axial angular velocities, and the product of the 3 axial angular velocities may be used as the composition value of the 3 axial angular velocities. In addition, instead of the composition value of the 3 axial angular velocities, the composition value of the 3 axial accelerations, such as the sum of squares or the square root of the 3 axial accelerations, the sum or the average of the 3 axial accelerations, and the product of the 3 axial accelerations, may be used.

In addition, in the embodiment, the acceleration sensor 12 and the angular velocity sensor 14 are embedded and integrated in the sensor unit 10. However, the acceleration sensor 12 and the angular velocity sensor 14 may not be integrated. Otherwise, the acceleration sensor 12 and the angular velocity sensor 14 may be directly mounted on the golf club 3 or the user 2 without being embedded in the sensor unit 10. In addition, in the embodiment, the sensor unit 10 and the motion analysis device 20 are separately provided, and the sensor unit 10 and the motion analysis device 20 may be integrated to be mounted on the golf club 3 or the user 2.

In addition, in the embodiment, the motion analysis system (motion analysis device) which analyzes golf swing is provided as an example. However, it is possible to apply the invention to a motion analysis system (motion analysis device) which analyzes swings of various motions such as tennis and baseball.

The above-described embodiment and the modification are examples, and the invention is not limited thereto. For example, it is possible to appropriately combine each embodiment and each modification example.

The invention includes a configuration (for example, a configuration which has the same function, method, and results or a configuration which has the same object and advantage) which is substantially the same as the configuration which is described in the embodiment. In addition, the invention includes a configuration in which a part of the configuration, which is described in the embodiment and which is not substantial, is replaced. In addition, the invention includes a configuration, which provides the same effect as the configuration described in the embodiment, or a configuration in which it is possible to accomplish the same object as the configuration described in the embodiment. In addition, the invention includes a configuration in which a well-known technology is added to the configuration described in the embodiment.

The entire disclosure of Japanese Patent Application No. 2014-136847, filed Jul. 2, 2014 is expressly incorporated by reference herein.

What is claimed is:

1. A motion analysis method comprising:
specifying a first axis along a longitudinal direction of a shaft section of sporting equipment when a user is at a standstill using an output of an inertial sensor; and
estimating a prescribed position between head and chest of the user when the user is at a standstill using the output of the inertial sensor and body information of the user, and specifying a second axis which connects the estimated prescribed position and a hitting position;
when a target ball-hitting direction is set to a third axis:
specifying a first virtual plane which includes the first axis and the third axis, and
specifying a second virtual plane which includes the second axis and the third axis;
acquiring information of locus of the sporting equipment based on a swing performed by the user;
determining whether the locus of the sporting equipment is between (a) a shaft plane which is the first virtual plane and is a plane that includes the longitudinal direction of the shaft of the sporting equipment at a standstill state and a target line in the ball-hitting direction and (b) a hogan plane which is the second virtual plane and includes a virtual line which connects peripheries of a shoulder of the user at a standstill state and a head of the sporting equipment, and the target line;
evaluating a straightness of the swing using the acquired information of the locus of the sporting equipment;
calculating a position of a grip end of the sporting equipment using the output of the inertial sensor; and
displaying, to the user and on a display unit, a graphical representation of the evaluated straightness of the swing,
wherein the specifying of the second axis includes estimating the prescribed position using the position of the grip end and a length of an arm of the user based on the body information.

2. The motion analysis method according to claim 1,
wherein the output of the inertial sensor includes acceleration information,
wherein the motion analysis method further comprises calculating an angle of inclination for a horizontal plane of the shaft section using the acceleration information when the user is at a standstill, and
wherein the specifying of the first axis includes specifying the first axis using the angle of inclination and information of a length of the shaft section.

3. The motion analysis method according to claim 1,
wherein the body information is the length of the arm of the user.

4. The motion analysis method according to claim 1,
wherein the prescribed position is on a line segment which connects both shoulders of the user.

5. The motion analysis method according to claim 1,
wherein the sporting equipment is provided with a ball-hitting surface, and
wherein the third axis is an axis in a direction which is perpendicular to the ball-hitting surface when the user is at a standstill.

6. The motion analysis method according to claim 1,
wherein the specifying of the first virtual plane includes calculating a width of the first virtual plane using the length of the shaft section and the length of the arm of the user based on the body information.

7. The motion analysis method according to claim 1, wherein the specifying of the second virtual plane includes calculating a width of the second virtual plane using the length of the shaft section and the length of the arm of the user based on the body information.

8. The motion analysis method according to claim 1, further comprising:
determining whether or not the locus is included between the first axis and the second axis.

9. The motion analysis method according to claim 1, further comprising:
generating image data which includes the first axis, the second axis, and the locus.

10. The motion analysis method according to claim 1, wherein the sporting equipment is a golf club.

11. A non-transitory, computer readable medium having stored thereon a program configured to:
specify a first axis along a longitudinal direction of a shaft section of sporting equipment when a user is at a standstill using an output of an inertial sensor;
estimate a prescribed position between head and chest of the user when the user is at a standstill using the output of the inertial sensor and body information of the user, and specify a second axis which connects the estimated prescribed position and a hitting position; and
when a target ball-hitting direction is set to a third axis:
specify a first virtual plane which includes the first axis and the third axis, and
specify a second virtual plane which includes the second axis and the third axis;
acquire information of locus of the sporting equipment based on swing performed by the user;
determine whether the locus of the sporting equipment is between (a) a shaft plane which is the first virtual plane and is a plane that includes the longitudinal direction of the shaft of the sporting equipment at a standstill state and a target line in the ball-hitting direction and (b) a hogan plane which is the second virtual plane and includes a virtual line which connects peripheries of a shoulder of the user at a standstill state and a head of the sporting equipment, and the target line;
evaluate a straightness of the swing using the acquired information of the locus of the sporting equipment;
calculate a position of a grip end of the sporting equipment using the output of the inertial sensor; and
display, to the user and on a display unit, a graphical representation of the evaluated straightness of the swing,
wherein the specifying of the second axis includes estimating the prescribed position using the position of the grip end and a length of an arm of the user based on the body information.

12. A motion analysis device comprising:
a first specification unit that specifies a first axis along a longitudinal direction of a shaft section of sporting equipment when a user is at a standstill using an output of an inertial sensor; and
a second specification unit that estimates a prescribed position between head and chest of the user when the user is at a standstill using the output of the inertial sensor and body information of the user, and specifies a second axis which connects the estimated prescribed position and a hitting part position,
wherein, when a target ball-hitting direction is set to a third axis:
the first specification unit specifies a first virtual plane which includes the first axis and the third axis and the second specification unit specifies a second virtual plane which includes the second axis and the third axis;
an acquisition unit that acquires information of locus of the sporting equipment based on swing performed by the user;
a determining unit that (1) determines whether the locus of the sporting equipment is between (a) a shaft plane which is the first virtual plane and is a plane that includes the longitudinal direction of the shaft of the sporting equipment at a standstill state and a target line in the ball-hitting direction and (b) a hogan plane which is the second virtual plane and includes a virtual line which connects peripheries of a shoulder of the user at a standstill state and a head of the sporting equipment, and the target line, and (2) evaluates a straightness of the swing using the acquired information of the locus of the sporting equipment;
a calculating unit that calculates a position of a grip end of the sporting equipment using the output of the inertial sensor; and
a display unit that displays, to the user, a graphical representation of the evaluated straightness of the swing,
wherein the specifying of the second axis includes estimating the prescribed position using the position of the grip end and a length of an arm of the user based on the body information.

* * * * *